(12) United States Patent
Flower et al.

(10) Patent No.: US 11,696,695 B2
(45) Date of Patent: Jul. 11, 2023

(54) QUANTIFICATION OF ABSOLUTE BLOOD FLOW IN TISSUE USING FLUORESCENCE MEDIATED PHOTOPLETHYSMOGRAPHY

(71) Applicant: Stryker European Operations Limited, Carrigtwohill (IE)

(72) Inventors: Robert W. Flower, Hunt Valley, MD (US); Robert Anthony Stead, Vancouver (CA); Arthur E. Bailey, North Vancouver (CA)

(73) Assignee: Stryker European Operations Limited, Carrigtwohill (IE)

( * ) Notice: Subject to any disclaimer, the term of this patent is extended or adjusted under 35 U.S.C. 154(b) by 712 days.

(21) Appl. No.: 16/588,584

(22) Filed: Sep. 30, 2019

(65) Prior Publication Data

US 2020/0100685 A1    Apr. 2, 2020

Related U.S. Application Data

(63) Continuation of application No. 14/510,848, filed on Oct. 9, 2014, now Pat. No. 10,426,361, which is a
(Continued)

(51) Int. Cl.
*A61B 5/0275* (2006.01)
*A61B 5/00* (2006.01)
*A61B 5/0295* (2006.01)

(52) U.S. Cl.
CPC .......... *A61B 5/0275* (2013.01); *A61B 5/0071* (2013.01); *A61B 5/0295* (2013.01); *A61B 5/6826* (2013.01)

(58) Field of Classification Search
CPC ... A61B 5/0275; A61B 5/0071; A61B 5/0295; A61B 5/6826
See application file for complete search history.

(56) References Cited

U.S. PATENT DOCUMENTS 6,236,881 B1 *  5/2001  Zahler ................. A61B 1/0638
                                                          600/476
6,577,884 B1    6/2003  Boas
(Continued)

FOREIGN PATENT DOCUMENTS

CN    103889328 A    6/2014
EP    2 910 185 A1    8/2015
(Continued)

OTHER PUBLICATIONS

Examination Report No. 1 dated Apr. 3, 2020, directed to AU Application No. 2019236680; 3 pages.
(Continued)

*Primary Examiner* — Jonathan Cwern
(74) *Attorney, Agent, or Firm* — Morrison & Foerster LLP

(57) ABSTRACT

A method and an apparatus for measuring a time-varying change in an amount of blood in a tissue include exciting a fluorescence agent in the blood, acquiring a time-varying light intensity signal during a pulsatile flow of the blood through the tissue volume, the pulsatile flow having a systolic and a diastolic phase resembling a conventional photoplethysmogram, and processing the acquired signal by applying a modified Beer-Lambert law to obtain the measurement of the time-varying change in the amount of blood in the tissue volume. The instantaneous molar concentration of the fluorescence agent is determined by utilizing a concentration-mediated change in a fluorescence emission spectrum of the fluorescence agent.

33 Claims, 29 Drawing Sheets

Related U.S. Application Data continuation-in-part of application No. 14/305,950, filed on Jun. 16, 2014, now Pat. No. 10,285,603.

(60) Provisional application No. 61/835,408, filed on Jun. 14, 2013.

(56) References Cited

U.S. PATENT DOCUMENTS

| | | | |
|---|---|---|---|
| 7,474,906 | B2 | 1/2009 | Rubinstein et al. |
| 8,285,353 | B2 | 10/2012 | Choi et al. |
| 8,718,747 | B2 | 5/2014 | Bjørnerud et al. |
| 9,451,903 | B2 | 9/2016 | Feinberg |
| 10,285,603 | B2 | 5/2019 | Flower |
| 10,311,567 | B2 | 6/2019 | Gurevich |
| 10,636,144 | B2 | 4/2020 | Gurevich |
| 10,646,128 | B2 | 5/2020 | Flower et al. |
| 2002/0007123 | A1 | 1/2002 | Balas |
| 2002/0111550 | A1* | 8/2002 | Schwamm ........... A61B 5/0263 600/431 |
| 2003/0127609 | A1 | 7/2003 | Hage et al. |
| 2005/0065432 | A1 | 3/2005 | Kimura |
| 2006/0011853 | A1 | 1/2006 | Spartiotis et al. |
| 2008/0188728 | A1 | 8/2008 | Neumann et al. |
| 2008/0221421 | A1 | 9/2008 | Choi et al. |
| 2009/0112097 | A1 | 4/2009 | Kato et al. |
| 2010/0000228 | A1 | 1/2010 | Rubinstein et al. |
| 2010/0003621 | A1 | 2/2010 | Choi et al. |
| 2010/0061604 | A1 | 3/2010 | Nahm et al. |
| 2010/0080757 | A1 | 4/2010 | Haaga et al. |
| 2010/0099961 | A1* | 4/2010 | Hubner ................ A61B 5/0285 600/504 |
| 2012/0323118 | A1 | 12/2012 | Menon Gopalakrishna et al. |
| 2014/0163403 | A1 | 6/2014 | Lenox et al. |
| 2014/0254909 | A1 | 9/2014 | Carmi et al. |
| 2014/0371583 | A1 | 12/2014 | Flower |
| 2015/0112192 | A1 | 4/2015 | Docherty et al. |
| 2015/0164396 | A1 | 6/2015 | Acharya et al. |
| 2015/0182137 | A1 | 7/2015 | Flower et al. |
| 2015/0248758 | A1 | 9/2015 | Pautot |
| 2015/0029708 | A1 | 10/2015 | Hong et al. |
| 2016/0253800 | A1 | 9/2016 | Gurevich et al. |
| 2017/0084024 | A1 | 3/2017 | Gurevich |
| 2017/0245766 | A1 | 8/2017 | Flower et al. |
| 2019/0035511 | A1 | 11/2019 | Gurevich et al. |
| 2020/0004051 | A1 | 12/2020 | Flower et al. |

FOREIGN PATENT DOCUMENTS

| | | | |
|---|---|---|---|
| JP | 2003-510121 | A | 3/2003 |
| JP | 2008-532682 | A | 8/2008 |
| JP | 2008-220926 | A2 | 9/2008 |
| JP | 2010-505582 | A | 2/2010 |
| JP | 2013-502263 | A | 1/2013 |
| WO | WO-90/12537 | A1 | 11/1990 |
| WO | WO-2009/127972 | A2 | 10/2009 |
| WO | WO-2011/021175 | A2 | 2/2011 |
| WO | WO-2015/001427 | A2 | 1/2015 |
| WO | WO-2015/041312 | A1 | 3/2015 |

OTHER PUBLICATIONS

Canadian Office Action dated Feb. 24, 2020 for Patent Application No. 2,998,699, filed Jul. 29, 2016, 3 pages.
Notice of Allowance dated Aug. 6, 2020, directed to CA Application No. 2,913,692; 1 page.
Chinese Notice of Allowance, Notification to Grant Patent Right for Invention dated Mar. 4, 2020 for Chinese Application No. 201480044769.1 filed on Jun. 16, 2014, 6 pages.
Extended European Search Report dated Jul. 16, 2019, for European Patent Application No. 17752595.3, filed Feb. 15, 2017, 13 pages.
Japanese Office Action dated Feb. 28, 2020, for Patent Application No. 2018-515609, filed Jul. 29, 2016, 6 pages.
Decision to Grant a Patent dated May 31, 2021, directed to JP Application No. 2020-109942; 6 pages.
Korean Office Action dated Jan. 8, 2020, for Korean Patent Application No. 10-2019-7033703, filed Jun. 16, 2014, 5 pages.
Notice of Allowance dated Oct. 30, 2020, directed to KR Application No. 10-2019-7033703; 3 pages.
U.S. Notice of Allowance dated Mar. 9, 2020, for U.S. Appl. No. 16/430,022, filed Jun. 30, 2019, eight pages.
Flower et al., U.S. Notice of Allowance and Fee(s) due dated Dec. 16, 2019, directed to U.S. Appl. No. 15/433,502; 7 pages.
Flower et al., U.S. Notice of Allowance and Fee(s) due dated Aug. 28, 2019, directed to U.S. Appl. No. 15/433,502; 8 pages.
Flower et al., U.S. Notice of Allowance and Fee(s) due dated Mar. 30, 2020, directed to U.S. Appl. No. 15/433,502; 7 pages.
Alm, A et al. (1973). "Ocular and Optic Nerve Blood Flow at Normal and Increased Intraocular Pressures in Monkeys (*Macaca irus*): A Study with Radioactively Labelled Microspheres including Flow Determinations in Brain and Some Other Tissues," *Experimental Eye Research* 15:15-29.
Australian Notice of Acceptance dated Jun. 12, 2019 for Australian Patent Application No. 2016325592 filed on Mar. 21, 2018, 3 pages.
Australian Office Action dated Jun. 28, 2018 for Australian Patent Application No. 2016325592 filed on Mar. 21, 2018, four pages.
Canadian Office Action dated Aug. 14, 2018 for Canadian Patent application No. 2,913,692 filed on Nov. 26, 2015, three pages.
Canadian Office Action dated Aug. 28, 2017 for Canadian Patent application No. 2,913,692 filed on Nov. 26, 2015, three pages.
Canadian Office Action dated Feb. 28, 2019 for Canadian Patent application No. 2,998,699 filed on Mar. 14, 2018, 9 pages.
Canadian Office Action dated Jul. 11, 2019, for Patent Application No. 2913692, filed on Nov. 26, 2015, 3 pages.
Canadian Office Action dated Nov. 4, 2016 for Canadian Patent application No. 2,913,692 filed on Nov. 26, 2015, five pages.
Chinese Office Action dated May 23, 2019 for Chinese Application No. 201480044769.1 filed on Jun. 16, 2014, 12 pages.
Chinese Office Action dated Nov. 4, 2018 for Chinese Application No. 201480044769.1 filed on Jun. 16, 2014, 10 pages.
Chinese Office Action dated Sep. 25, 2019 for Chinese Application No. 201480044769.1 filed on Jun. 16, 2014, 10 pages.
Elgendi, M. (Feb. 2012). "On the Analysis of Fingertip Photoplethysmogram Signals," *Current Cardiology Reviews* 8(1):14-25.
Eren, S. et al. (Dec. 1995). "Assessment of Microcirculation of an Axial Skin Flap Using Indocyanine Green Fluorescence Angiography," *Plastic and Reconstructive Surgery* 96(7):1636-1649.
European Communication Pursuant to Rules 70(2) and 70a(2) EPC dated May 23, 2017 for EP Application No. 14820367.2, filed on Nov. 25, 2015, one page.
European Extended Search Report dated May 4, 2017 for EP Application No. 14820367.2, filed on Nov. 25, 2015, ten pages.
European Office Action dated Mar. 19, 2019 for EP Application No. 14820367.2, filed on Nov. 25, 2015, 6 pages.
European Office Action mailed on May 18, 2018 for EP Application No. 14820367.2, filed on Nov. 25, 2015, five pages.
European Supplementary Partial Search Report dated Jan. 20, 2017 for EP Application No. 14820367.2, filed on Nov. 25, 2015, seven pages.
Flower, R.W. (Dec. 1973). "Injection Technique for Indocyanine Green and Sodium Fluorescein Dye Angiography of the Eye," *Investigative Ophthalmology* 12:881-895.
Flower, R.W. et al. (Aug. 1977). "Quantification of Indicator Dye Concentration in Ocular Blood Vessels," *Exp. Eye Res.* 25(2):103-111.
Humphreys, K. et al. (2007; e-published Apr. 23, 2007). "Noncontract Simultaneous Dual Wavelength Photoplethysmogrphy: A Further Step Toward Noncontract Pulse Oximetry," *Review of Scientific Instruments* 78:044304, six pages.
International Preliminary Report on Patentability dated Apr. 5, 2018 for International Application No. PCT/IB2016/001216 filed on Jul. 29, 2016, six pages.
International Preliminary Report on Patentability dated Aug. 30, 2018 for International Application No. PCT/CA2017/050189 filed on Feb. 15, 2017, seven pages.

(56) References Cited

OTHER PUBLICATIONS

International Search Report and Written Opinion dated Dec. 28, 2016 for International Application No. PCT/IB2016/001216 filed on Jul. 29, 2016, eight pages.
International Search Report and Written Opinion dated Feb. 5, 2015 for International Application No. PCT/IB2014/002184 filed on Jun. 16, 2014, eleven pages.
International Search Report and Written Opinion dated May 11, 2017, for International Application No. PCT/CA2017/050189, filed on Feb. 15, 2017, eleven pages.
Japanese Notice of Allowance dated Feb. 16, 2018 for Japanese Patent Application No. 2016-518598 filed on Dec. 9, 2015, six pages.
Japanese Office Action dated Jul. 1, 2019, for Patent Application No. 2018-515609, filed on Jul. 29, 2016, 9 pages.
Japanese Office Action dated Nov. 14, 2016 for Japanese Patent Application No. 2016-518598 filed on Dec. 9, 2015, five pages.
Japanese Office Action dated Jun. 30, 2017 for JP Application No. 2016-518598, filed on Dec. 9, 2015, four pages.
Jayanthy, A.K. et al. (Feb. 2011). "Measuring Blood Flow: Techniques and Applications—A Review," *IJRRAS* 6(2):203-216.
Korean Office Action dated Jan. 28, 2019 for KR Application No. 10-2016-7000943 filed on Jan. 13, 2016, 5 pages.
Korean Office Action dated Jun. 27, 2018 for KR Application No. 10-2016-7000943 filed on Jan. 13, 2016, four pages.
Korean Office Action dated May 13, 2019 for KR Application No. 10-2016-7000943 filed on Jan. 13, 2016, 8 pages.
Korean Office Action dated Oct. 19, 2017 for KR Application No. 10-2016-7000943 filed on Jan. 13, 2016, ten pages.
Maarek, J.I. et al. (Mar. 1, 2007). "Fluorescence Dilution Technique for Measurement of Cardiac Output and Circulating Blood Volume in Healthy Human Subjects," *Anesthesiology* 106(3):491-498.
Mitra, S. et al. (Sep. 1, 2003). "Serial Determinations of Absolute Plasma Volume with Indocyanine Green During Hemodialysis," *Journal of American Society of Nephrology (JASN)* 14:2345-2351.
Nadler, S.B. et al. (Feb. 1962). "Prediction Of Blood Volume In Normal Human Adults," *Surgery* 51 (2):224-232.
Nunan, R. et al. (2014). "Clinical Challenges of Chronic Wounds: Searching for an Optimal Animal Model to Recapitulate their Complexity," *The Company of Biologists—Disease Models & Mechanisms* 7:1205-1213.
Stadler, I. et al. (Jul.-Aug. 2004). "Development of a simple, noninvasive, clinically relevant model of pressure ulcers in the mouse," *Journal of Investigative Surgery* 17(4):221-227.
U.S. Final Office Action dated Apr. 12, 2019, for U.S. Appl. No. 15/433,502, filed Feb. 15, 2017, seven pages.
U.S. Final Office Action dated Jul. 14, 2017, for U.S. Appl. No. 14/305,950, filed Jun. 16, 2014, thirteen pages.
U.S. Final Office Action dated Jul. 20, 2018, for U.S. Appl. No. 15/224,088, filed Jul. 29, 2016, seven pages.
U.S. Final Office Action dated Jun. 22, 2017, for U.S. Appl. No. 14/510,848, filed Oct. 9, 2014, fourteen pages.
U.S. Non Final Office Action dated Feb. 23, 2018, for U.S. Appl. No. 15/224,088, filed Jul. 29, 2016, nineteen pages.
U.S. Non Final Office Action dated Jun. 28, 2018, for U.S. Appl. No. 14/510,848, filed Oct. 9, 2014, eighteen pages.
U.S. Non Final Office Action dated Sep. 17, 2018, for U.S. Appl. No. 15/433,502, filed Feb. 15, 2017, eleven pages.
U.S. Non Final Office Action dated Sep. 22, 2016, for U.S. Appl. No. 14/305,950, filed Jun. 16, 2014, nine pages.
U.S. Non Final Office Action dated Sep. 28, 2016, for U.S. Appl. No. 14/510,848, filed Oct. 9, 2014, twenty pages.
U.S. Non-Final Action dated Sep. 6, 2019, for U.S. Appl. No. 16/430,022, filed Jun. 30, 2019, 14 pages.
U.S. Notice of Allowance dated Dec. 12, 2018, for U.S. Appl. No. 15/224,088, filed Jul. 29, 2016, nine pages.
U.S. Notice of Allowance dated Dec. 28, 2018, for U.S. Appl. No. 14/305,950, filed Jun. 16, 2014, ten pages.
U.S. Notice of Allowance dated Mar. 27, 2019, for U.S. Appl. No. 14/510,848, filed Oct. 9, 2014, 10 pages.
U.S. Appl. No. 16/430,022, filed Jun. 3, 2019, by Gurevich et al. (U.S. Patent Application is not submitted herewith pursuant to the waiver of 37 C.F.R. § 1.98(a)(2)(iii) issued by the Office on Sep. 21, 2004.).
Office Action dated Sep. 20, 2022, directed to EP Application No. 17 752 595.3; 5 pages.
Flower et al., U.S. Office Action dated Oct. 11, 2022, directed to U.S. Appl. No. 16/872,321; 9 pages.
First Office Action dated May 27, 2021, directed to CN Application No. 201680068429.1; 29 pages.
Notification to Grant Patent Right for Invention dated Feb. 23, 2022, directed to CN Application No. 201680068429.1; 9 pages.
Extended European Search Report dated Mar. 15, 2019, directed to EP Application No. 16848206.5; 12 pages.
Office Action dated Jun. 22, 2022, directed to EP Application No. 16848206.5; 5 pages.
Flower et al., U.S. Office Action dated Apr. 6, 2022, directed to U.S. Appl. No. 16/872,321; 10 pages.

* cited by examiner

Red and Infrared Diodes

FIG. 11A
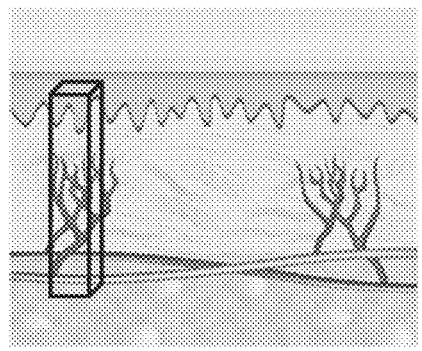
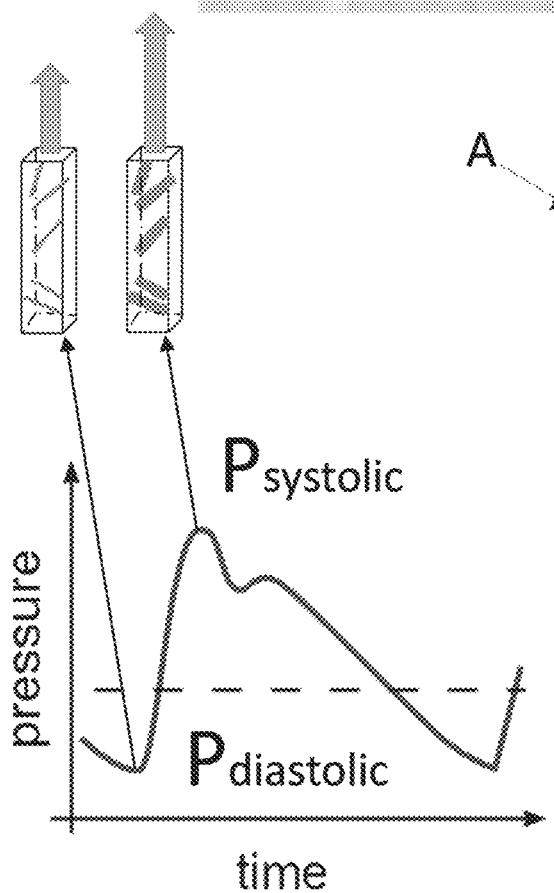
FIG. 11B
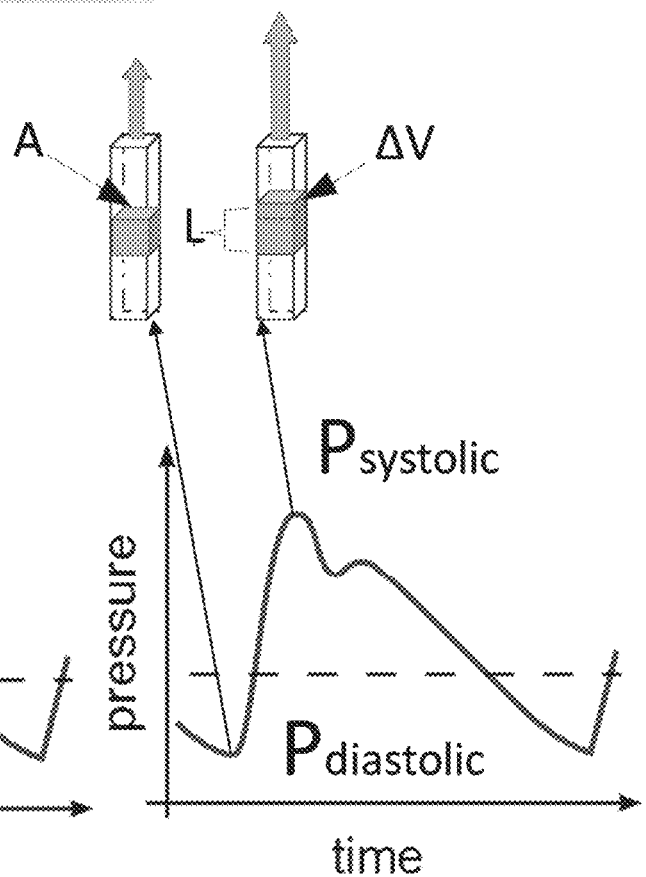
FIG. 11C

QUANTIFICATION OF ABSOLUTE BLOOD
FLOW IN TISSUE USING FLUORESCENCE
MEDIATED PHOTOPLETHYSMOGRAPHY

CROSS-REFERENCE TO RELATED APPLICATIONS

This is a continuation of U.S. patent application Ser. No. 14/510,848, filed on Oct. 9, 2014, now U.S. Pat. No. 10,426,361, which is a continuation-in-part of U.S. patent application Ser. No. 14/305,950, filed on Jun. 16, 2014, now U.S. Pat. No. 10,285,603, which claims the benefit of U.S. Provisional Application No. 61/835,408, filed on Jun. 14, 2013. The disclosures of the prior applications are hereby incorporated by reference herein in their entirety.

TECHNICAL FIELD

The present disclosure relates generally to the field of optical assessment of blood flow in tissue using photoplethysmography (PPG), and in particular to the quantitative assessment of blood flow in tissue, including microvascular blood flow in tissue.

BACKGROUND

Perfusion refers to the flow of blood into and out of the tissue capillary bed. Quantification of tissue perfusion is of interest to clinicians across many surgical and non-surgical specialties. Although simple binary assessment (flow versus no-flow) may be adequate for some clinical applications, quantification of perfusion in standard measures is desirable in many other clinical applications. To date, quantitative assessment of tissue perfusion has remained elusive.

Photoplethysmography (PPG) is an optical technique that can be used to estimate changes in microvascular blood volume, and PPG-based technology has been deployed in commercially available medical devices for assessing pulse rate, oxygen saturation, blood pressure, and cardiac output. A typical output of such devices is the PPG waveform that corresponds to the heartbeat of the subject. Despite the relatively wide application of PPG technology to such medical devices, PPG has not been utilized to provide measurements in standardized units when assessing blood flow. A PPG technology with such capabilities would enable routine measurements of blood flow in tissue, including perfusion measurements, to be made in standardized units of volume/unit time/tissue area. This would be of significant value to clinicians, as such measurements would allow direct inter-site and inter-subject comparisons.

SUMMARY

In accordance with one aspect of the disclosure, there is provided a method for measuring a time-varying change in an amount of blood in a tissue volume. The method includes exciting a fluorescence agent such as for example indocyanine green (ICG) in the blood, acquiring a time-varying light intensity signal during a pulsatile flow of the blood through the tissue volume, wherein the pulsatile flow has a diastolic and a systolic phase resembling a conventional photoplethysmogram, and processing the acquired time-varying light intensity signal to obtain a measurement of the time-varying change in the amount of blood in the tissue volume.

In accordance with another aspect, there is provided an apparatus for measuring a time-varying change in an amount of blood in a tissue volume. The apparatus includes a light source configured to excite a fluorescence agent such as for example ICG in the blood, a sensor configured to acquire a time-varying light intensity signal during a pulsatile flow of the blood through the tissue volume, wherein the pulsatile flow has a diastolic and a systolic phase resembling a conventional photoplethysmogram, and a processor configured to process the acquired time-varying light intensity signal to obtain a measurement of the time-varying change in the amount of blood in the tissue volume.

In the various aspects of the method and the apparatus, a modified Beer Lambert law is applied at the diastolic and systolic phases of the pulsatile flow of blood through tissue volume such that $\Delta L=\ln[(I_e\Phi-I_m)/(I_e\Phi-I_p)](\varepsilon C)^{-1}$ where $\Delta L$ is a change in aggregate blood layer thickness within a given tissue volume, $I_e$ is an intensity of an excitation light exciting the fluorescence agent in the blood, $\Phi$ is a quantum efficiency of the fluorescence agent, $I_m$ is an intensity of the time-varying light intensity signal during the diastolic phase minimum of the pulsatile flow of the blood through the tissue volume, $I_p$ is an intensity of the time-varying light intensity signal during the systolic phase maximum of the pulsatile flow of the blood through the tissue volume, $\varepsilon$ is a molar absorption coefficient for the fluorescence agent, and $C$ is an instantaneous molar concentration of the fluorescence agent in the blood.

In the various aspects of the method and the apparatus, the instantaneous molar concentration of the fluorescence agent in the blood is determined by utilizing a concentration-mediated change in a fluorescence emission spectrum of the fluorescence agent. The concentration-mediated change in fluorescence emission spectrum of the fluorescence agent includes a monotonic spectral shift.

In various aspects of the method and the apparatus, utilizing the concentration-mediated change in fluorescence emission spectrum of the fluorescence agent includes selecting first and second spectral bands of fluorescence emission spectrum of the fluorescence agent, acquiring first and second intensities of fluorescence emission integrated over wavelengths in the first and second spectral bands respectively, calculating a ratio of the first and second intensities, and deriving a value for C from the ratio. In various embodiments, the first spectral band includes wavelengths ranging from about 780 nm to about 835 nm, or a subset thereof, and the second spectral band includes wavelengths ranging from about 835 nm to about 1000 nm, or a subset thereof.

According to an embodiment, the first and second spectral bands are selected such that one of the first and second intensities varies monotonically with C, and one of the first and second intensities is unchanged with C. In another embodiment, the first and second spectral bands are selected such that the first and second intensities increase monotonically with C, but at different rates. In yet further embodiment, the first and second spectral bands are selected such that the first intensity increases monotonically with C, and the second intensity decreases monotonically with C. The instantaneous molar concentration of the fluorescence agent in blood ranges in various embodiments from about 2 μM to about 10 mM.

BRIEF DESCRIPTION OF THE DRAWINGS

In accompanying drawings which illustrate embodiments of the disclosure,

FIGS. 11A, 11B, and 11C schematically illustrate the time-varying changes in an amount of blood in a tissue volume with phases of the cardiovascular pulse;

DETAILED DESCRIPTION OF THE EMBODIMENTS

Reference will now be made in detail to implementations and embodiments of various aspects and variations of the disclosure, examples of which are illustrated in the accompanying drawings.

Figure 1:
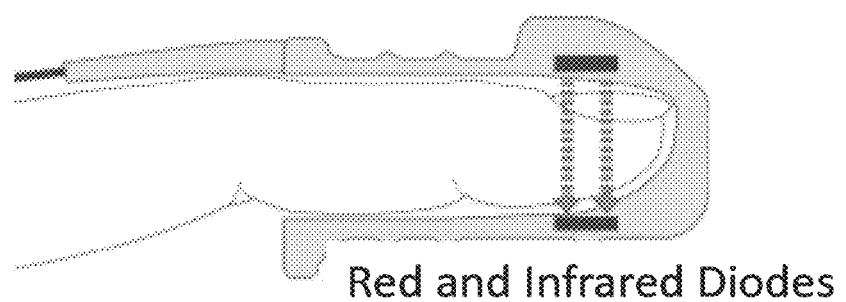
FIG. 1 schematically illustrates the use of conventional photoplethysmography (PPG) in which a fingertip sensor is used to measure pulse rate, blood oxygen saturation or both.
Figure 1:
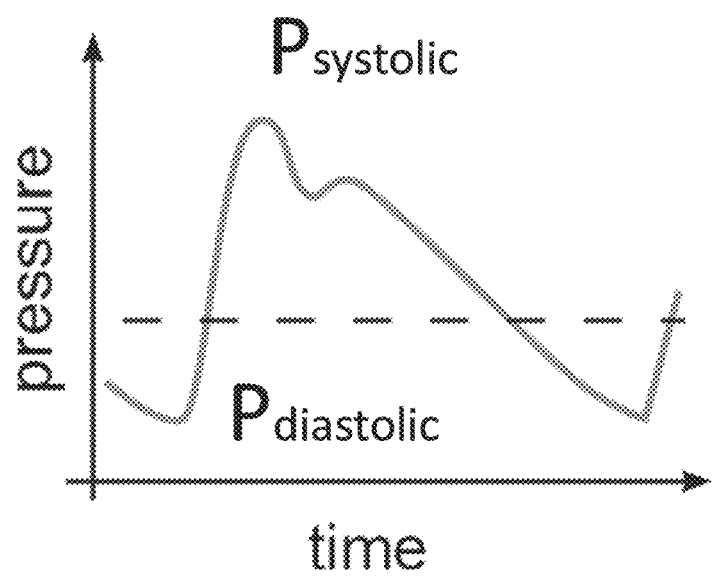

Conventional photoplethysmography (PPG) can estimate changes in tissue blood volume by detecting changes in the amount of red or near-infrared light transmitted through the tissue. As the blood volume within tissue expands and contracts during a cardiovascular pressure pulse corresponding to the heartbeat of the subject, the amount of light absorbed by the blood volume increases and decreases, respectively. As shown in FIG. 1, for example, the aggregate blood volume in the fingertip blood vessels is smallest during cardiovascular pressure pulse diastole and the volume is greatest during systole. Although it may be used for measuring pulse rate and blood oxygenation, this application of PPG technology is not configured to provide volumetric flow measurements in standardized units.

To be able to provide volumetric microvascular blood flow measurements in standardized units, the metrics of the PPG waveform must be related in a known and repeatable fashion to the blood volume changes in the tissue. It is possible to establish this type of deterministic relationship with the application of a modified Beer-Lambert law (also known as Beer's law, or the Beer-Lambert-Bouguer law). The Beer-Lambert law relates the attenuation of a light beam passing through a medium to the path length through the medium and its absorptivity and this relationship is utilized in conventional PPG. Conventional PPG is performed by passing a beam of near-IR wavelengths of light through tissue (e.g., a fingertip), but the need for trans-illumination of tissue significantly limits application of this method to the more general case of volumetric blood flow measurements in tissue. According to an embodiment, the present disclosure utilizes a modified Beer-Lambert law to enable such blood flow measurements using fluorescent light wavelengths emitted by a fluorescence agent such as a fluorescence dye. Such a dye may, for example, be bound preferentially to blood plasma, thereby making it possible to position both the light beam source and fluorescent light detector on the surface of the tissue. The fluorescent light emitted from, for example, the dye-tagged plasma component of blood will conform to the modified Beer-Lambert law and, by solving the equation for the optical path length and quantifying the respective parameters, fluorescence-mediated PPG is capable of providing volumetric blood flow measurements, including microvascular blood flow measurements without trans-illumination.

Thus, in contrast to the conventional PPG technology, the present disclosure provides fluorescence-mediated photoplethysmography (FM-PPG) for measuring time-varying changes in the amount of blood in a tissue volume, and presenting these changes as a blood flow, including microvascular blood flow, in standardized units (e.g., volume/unit time). With FM-PPG, according to the various embodiments, the detected fluorescence intensity is proportional to the instantaneous concentration of a fluorescence agent in the blood (e.g., a fluorescence agent in the blood plasma), and can thus be utilized to determine blood flow in tissue, including microvascular blood flow or perfusion. Blood flow in tissue is generally understood as an increase in the total amount of blood flowing into an anatomic structure or region; blood flow encompasses tissue perfusion or microvascular blood flow, which is the amount of blood flowing through the capillaries of the vascular bed of the anatomic structure or region. In various embodiments, the method and apparatus of the present disclosure are used for measuring blood flow in tissue, and more particularly, for measuring perfusion or microvascular blood flow in tissue. In various embodiments, the use of the method and apparatus of the present disclosure includes the ability to discriminate between the blood flow and the microvascular blood flow.

In accordance with one aspect of the disclosure, there is provided a method for measuring a time-varying change in an amount of blood in a tissue volume. The method comprises exciting a fluorescence agent in the blood, acquiring a time-varying light intensity signal, which includes a time-varying fluorescence intensity signal, during a pulsatile flow of the blood through the tissue volume, the pulsatile flow having a diastolic phase and a systolic phase resembling a conventional photoplethysmogram. The method further comprises processing the acquired time-varying light intensity signal to obtain a measurement of the time-varying change in the amount of blood in the tissue volume by applying a modified Beer-Lambert law at the diastolic and systolic phases.

In various embodiments, a suitable fluorescence agent is an agent which can circulate with the blood (e.g., an agent which can circulate with, for example a component of the blood such as plasma in the blood) and which fluoresces when exposed to appropriate excitation light energy. Furthermore, the fluorescence agent exhibits a concentration-mediated change in its fluorescence emission spectrum. In various embodiments, the concentration-mediated change includes a monotonic spectral shift in the fluorescence emission spectrum of the fluorescence agent. An example of the fluorescence agent is a fluorescence dye, which includes any non-toxic fluorescence dye exhibiting a monotonic spectral shift with concentration. In certain embodiments, the fluorescence dye is a dye that emits light in the near-infrared spectrum. In certain embodiments, the fluorescence dye is a tricarbocyanine dye such as, for example, indocyanine green (ICG). In other embodiments the fluorescence dye may further comprise fluorescein isothiocyanate, rhodamine, phycoerythrin, phycocyanin, allophycocyanin, o-phthaldehyde, fluorescamine, rose Bengal, trypan blue, fluoro-gold, or a combination thereof, using excitation light wavelengths appropriate to each dye. In some embodiments, an analogue or a derivative of the fluorescence dye may be used. For example, a fluorescence dye analog or a derivative includes a fluorescence dye that has been chemically modified, but still retains its ability to fluoresce when exposed to light energy of an appropriate wavelength.

One aspect of the method of measuring the time-varying change in the amount of blood in the tissue volume of the subject comprises administering the fluorescence agent to the subject such that the fluorescence agent circulates with the blood in the tissue volume as the blood flows through the tissue volume. In various embodiments, the fluorescence agent may be administered to the subject intravenously, e.g., as a bolus injection, in a suitable concentration for imaging. In various embodiments, the fluorescence agent may be injected into a vein, artery, microvasculature (e.g., a capillary bed) or a combination thereof of the subject such that it circulates in the microvasculature. In embodiments in which multiple fluorescence agents are used, such agents may be administered simultaneously, e.g. in a single bolus, or sequentially, e.g. in separate boluses. In some embodiments, the fluorescence agent may be administered by a catheter. In certain embodiments, the fluorescence agent may be administered to the subject less than an hour in advance of performing the measurement according to the various embodiments. For example, the fluorescence agent may be administered to the subject less than 30 minutes in advance of the measurement. In yet other embodiments, the fluorescence agent may be administered at least 30 seconds in advance of performing the measurement. In still other embodiments, the fluorescence agent may be administered contemporaneously with performing the measurement as described in connection with the various embodiments.

The fluorescence agent may be provided as a lyophilized powder, solid, or liquid. In certain embodiments, the fluorescence agent may be provided in a vial (e.g., a sterile vial), which may permit reconstitution to a suitable concentration by administering a sterile fluid with a sterile syringe. Reconstitution may be performed using any appropriate carrier or diluent. For example, the fluorescence agent may be reconstituted with water immediately before administration. In various embodiments, any diluent or carrier which will maintain the fluorescence agent in solution may be used. As an example, in certain embodiments where the fluorescence agent is ICG, it may be reconstituted with water. In some embodiments, once the fluorescence agent is reconstituted, it may be mixed with additional diluents and carriers. In some embodiments, the fluorescence agent may be conjugated to another molecule, e.g., a protein, a peptide, an amino acid, a synthetic polymer, or a sugar e.g., to enhance solubility, stability, imaging properties or a combination thereof. Additional buffering agents may optionally be added including Tris, HCl, NaOH, phosphate buffer, HEPES.

In various embodiments, the fluorescence agent may be administered in various concentrations to achieve a desired circulating concentration in the blood. For example, when the fluorescence agent is ICG, it may be administered at a concentration of about 2.5 mg/mL to achieve a circulating concentration of about 5 µM to about 10 µM in blood. In various embodiments, the upper concentration limit for the administration of the fluorescence agent is the concentration at which the fluorescence agent becomes clinically toxic in circulating blood, and the lower concentration limit is the instrumental detection limit for detecting the fluorescence agent in circulating blood. In various other embodiments, the upper concentration limit for the administration of the fluorescence agent is the concentration at which the fluorescence agent becomes self-quenching. In further embodiments, a lower concentration limit for the administration of the fluorescence agent is the concentration at which the fluorescence agent becomes too difficult for conventional imaging technology to detect. For example, when the fluorescence agent is ICG, the circulating concentration of the fluorescence agent may range from 2 µM to about 10 mM.

The method for measuring the time-varying change in the amount of blood in the tissue volume further comprises acquiring the time-varying light intensity signal during the pulsatile flow of the blood through the tissue volume. In various embodiments, the pulsatile flow arises from a cardiovascular pressure pulse, which may be generated by a heartbeat or simulated heartbeat (e.g., by using a blood pump. The pulsatile flow comprises a diastolic phase and a systolic phase. Furthermore, the diastolic and systolic phases resemble a conventional photoplethysmogram.

The method yet further comprises processing the acquired time-varying light intensity signal (e.g., a time-varying fluorescent light intensity signal) to provide a measurement of the time-varying change in the amount of blood in the tissue volume wherein a modified Beer-Lambert law is applied at the diastolic and systolic phases. The modified Beer-Lambert law for emitted fluorescence light may be written as: $\Delta L = \ln[(I_e\Phi - I_m)/(I_e\Phi - I_p)](\varepsilon C)^{-1}$ wherein $\Delta L$ is a change in aggregate blood layer thickness within a given tissue volume, $I_e$ is an intensity of an excitation light exciting the fluorescence agent, $\Phi$ is a quantum efficiency of the fluorescence agent, $I_m$ is an intensity of the time-varying light intensity signal during the diastolic phase minimum of the pulsatile flow of the blood through the tissue volume, $I_p$ is an intensity of the time-varying light intensity signal during the systolic phase maximum of the pulsatile flow of the blood through the tissue volume, $\varepsilon$ is a molar absorption coefficient for the fluorescence agent, and C is an instantaneous molar concentration of the fluorescence agent in the blood.

Figure 2:
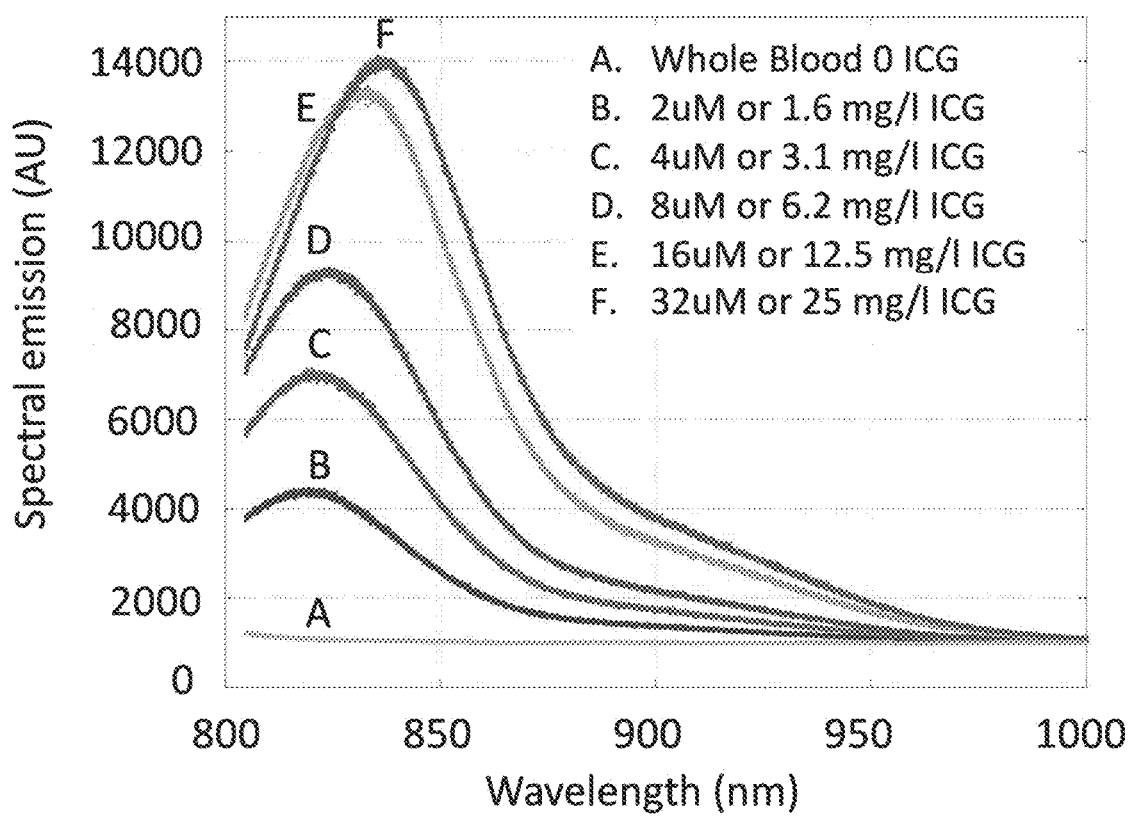
FIG. 2 shows fluorescence emission spectra of indocyanine green (ICG) dye shifting to longer wavelengths with increasing molar concentration of the dye in blood according to an embodiment.

As demonstrated in FIG. 2, the emission spectrum for ICG dye in whole blood is different for each different molar concentration of the dye. In various embodiments, the instantaneous molar concentration of the fluorescence agent is determined by utilizing a concentration-mediated change in a fluorescence emission spectrum of the fluorescence agent. The concentration-mediated change includes a monotonic spectral shift in the fluorescence emission spectrum of the fluorescence agent.

Figure 3:
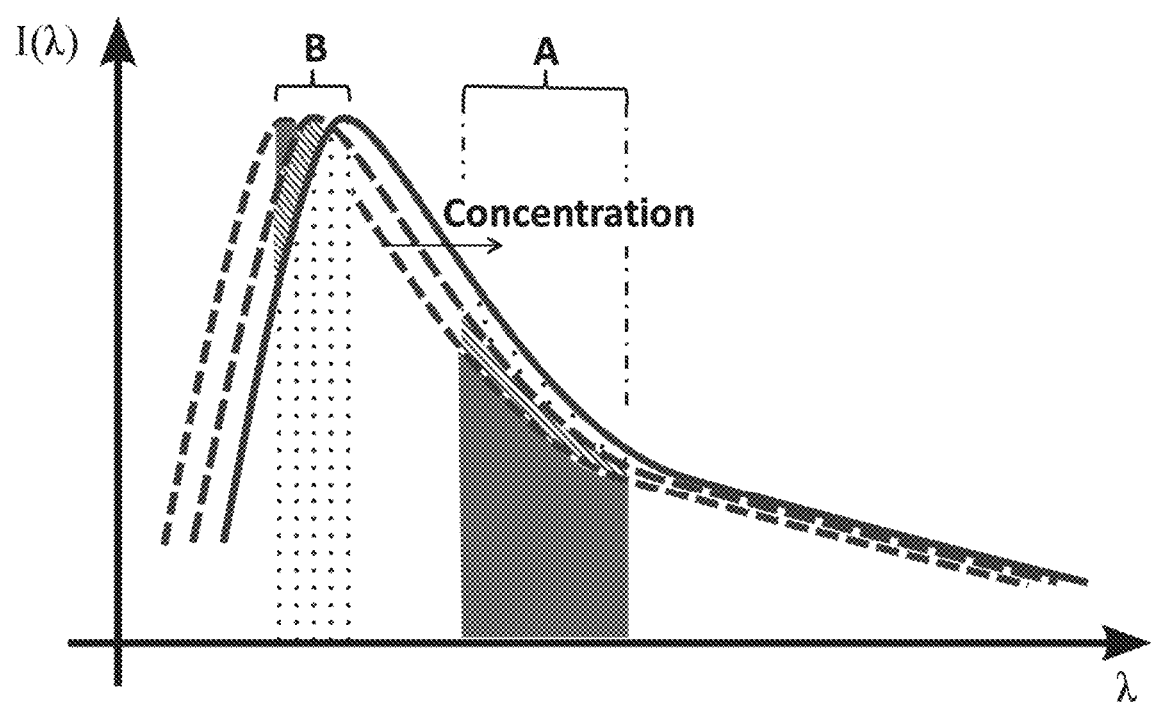
FIG. 3 illustrates an embodiment in which an instantaneous molar concentration of the fluorescence agent in the blood is determined by utilizing a spectral shift in the fluorescence emission spectrum of the fluorescence agent where first and second spectral bands are selected such that one of the first and second intensities varies monotonically with concentration, and one of the first and second intensities is unchanged with concentration.

In various embodiments, utilizing the concentration-mediated change in the fluorescence emission spectrum of the fluorescence agent comprises selecting first and second spectral bands of a fluorescence emission spectrum of the fluorescence agent (e.g., as is shown in FIG. 3), acquiring first and second intensities of fluorescence emission integrated over wavelengths in the first and second spectral bands respectively, calculating a ratio of the first and second intensities, and deriving a value for C in the modified Beer-Lambert law from the calculated ratio.

In various embodiments, the first and second spectral bands may be selected in a number of ways. According to an embodiment, the first and second spectral bands are selected such that one of the first and second intensities varies (increases or decreases) monotonically with C, and one of the first and second intensities is unchanged with C. For example, as is illustrated in FIG. 3, the intensity of fluorescence emission integrated over wavelengths for any bands selected in range B will remain nominally unchanged with increasing concentration of the fluorescence agent. Furthermore, the intensity of fluorescence emission integrated over wavelengths for any bands selected in range A will decrease with C. Consequently, the ratio of intensities of bands from A/B will decrease with C.

Figure 4:
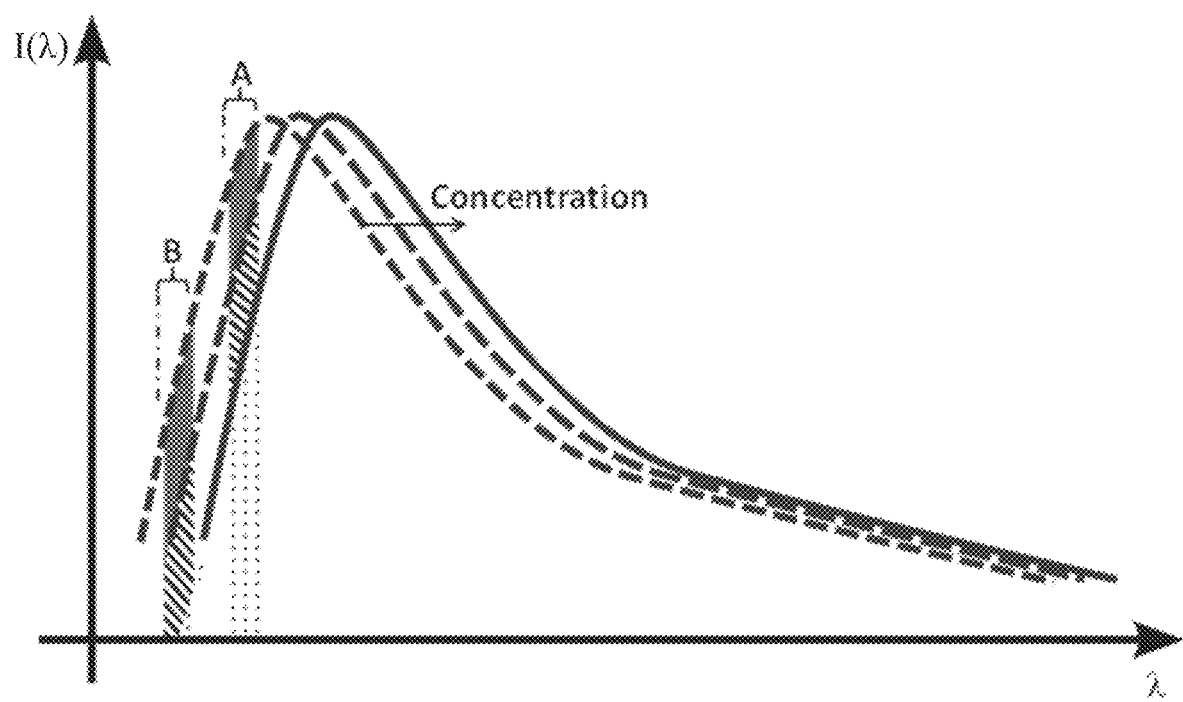
FIG. 4 illustrates an embodiment in which an instantaneous molar concentration of the fluorescence agent in the blood is determined by utilizing a spectral shift in the fluorescence emission spectrum of the fluorescence agent where first and second spectral bands are selected such that the first and second intensities increase monotonically with concentration, but at different rates.

According to another embodiment, the first and second spectral bands are selected such that the first and second intensities decrease monotonically with C, but at different rates. For example, as is illustrated in FIG. 4, the intensity of fluorescence emission integrated over wavelengths for any bands selected in range B will decrease with C, but the intensity of fluorescence emission integrated over wavelengths for any bands selected in range A will decrease more slowly with C. Consequently, the ratio of intensities of bands from A/B will decrease with C.

Figure 5:
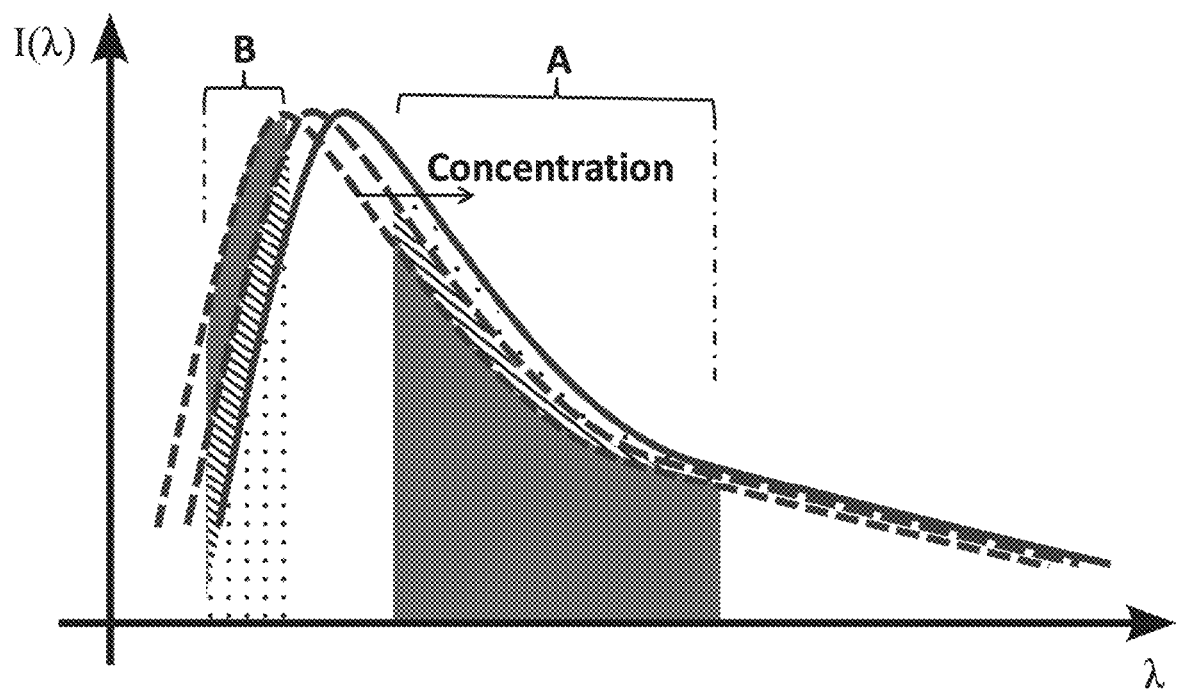
FIG. 5 illustrates an embodiment in which an instantaneous molar concentration of the fluorescence agent in the blood is determined by utilizing a spectral shift in the fluorescence emission spectrum of the fluorescence agent where first and second spectral bands are selected such that the first intensity increases monotonically with concentration, and the second intensity decreases monotonically with concentration.

According to yet another embodiment, the first and second spectral bands are selected such that the first intensity increases monotonically with C, and the second intensity decreases monotonically with C. For example, as is illustrated in FIG. 5, the intensity of fluorescence emission integrated over wavelengths for any bands selected in range B will increase with C, but the intensity of fluorescence emission integrated over wavelengths for any bands selected in range A will decrease with C. Consequently, the ratio of intensities of bands from A/B will decrease with C, but will do so at a greater rate than in the previous embodiments.

In various embodiments, the first spectral band comprises wavelengths ranging from about 780 nm to about 835 nm, or a subset thereof, and the second spectral band comprises wavelengths ranging from about 835 nm to about 1000 nm, or a subset thereof when, for example, the fluorescence agent is ICG.

By selecting the first and second spectral bands as described in connection with the various embodiments, a clinically discernible variation in the ratio is achieved over the range of clinically anticipated concentrations of the fluorescence agent in the circulating blood, and thus the instantaneous molar concentration, C, of the fluorescence agent can be determined.

In various embodiments, the method may further comprise correlating the measurement of the time-varying change in the amount of blood in the tissue volume to a biological parameter, a physiological parameter, a diagnostic parameter, a pathological parameter or a combination thereof. In an alternative embodiment, the method may comprise deriving a measurement of a change in a biological parameter, a physiological parameter, a diagnostic parameter, a pathological parameter or a combination thereof from the measurement of the time-varying change in the amount of blood in the tissue volume. In various embodiments, examples of the biological parameter, the physiological parameter, the diagnostic parameter, the pathological parameter or a combination thereof include those which are indicative or a certain condition of the tissue, a condition of the subject or a combination thereof (e.g., atherosclerosis, oxygenation, cardiac output).

In accordance with another aspect of the disclosure, there is provided an apparatus for measuring the time-varying change in an amount of blood in the tissue volume. The apparatus comprises a light source configured to excite the fluorescence agent in the blood, a sensor configured to acquire the time-varying light intensity signal during the pulsatile flow of the blood through the tissue volume (where the pulsatile flow may be caused, for example, by a heartbeat or by means simulating the heartbeat such as, for example, a blood pump), the pulsatile flow having a diastolic and a systolic phase resembling a conventional photoplethysmogram, and a processor configured to process the acquired time-varying light intensity signal to obtain a measurement of the time-varying change in the amount of blood in the tissue volume. A modified Beer-Lambert law is applied at the diastolic and systolic phases to obtain $\Delta L = \ln[(I_e\Phi - I_m)/(I_e\Phi - I_p)](\varepsilon C)^{-1}$ as was described in connection with the method embodiments.

In various embodiments of the apparatus, the instantaneous molar concentration of the fluorescence agent, C, is determined by a utilization of a concentration-mediated change, including a monotonic spectral shift, in a fluorescence emission spectrum of the fluorescence agent. In various embodiments, the utilization comprises a selection of first and second spectral bands of fluorescence emission spectrum of the fluorescence agent, an acquisition of first and second intensities of fluorescence emission integrated over wavelengths in the first and second spectral bands respectively, a calculation of a ratio of the first and second intensities, and a derivation of a value for C from the ratio.

According to an embodiment, the selection of the first and second spectral bands is such that one of the first and second intensities varies monotonically with C, and one of the first and second intensities is unchanged with C. According to another embodiment, the first and second intensities increase monotonically at different rates with C. According to yet another embodiment, the first intensity increases monotonically with C, and the second intensity decreases monotonically with C. Examples relating to these embodiments are illustrated in FIGS. 3 to 5. In various embodiments, the first spectral band comprises wavelengths ranging from about 780 nm to about 835 nm, or a subset thereof, and the second spectral band comprises wavelengths ranging from about 835 nm to about 1000 nm, or a subset thereof.

Figure 6:
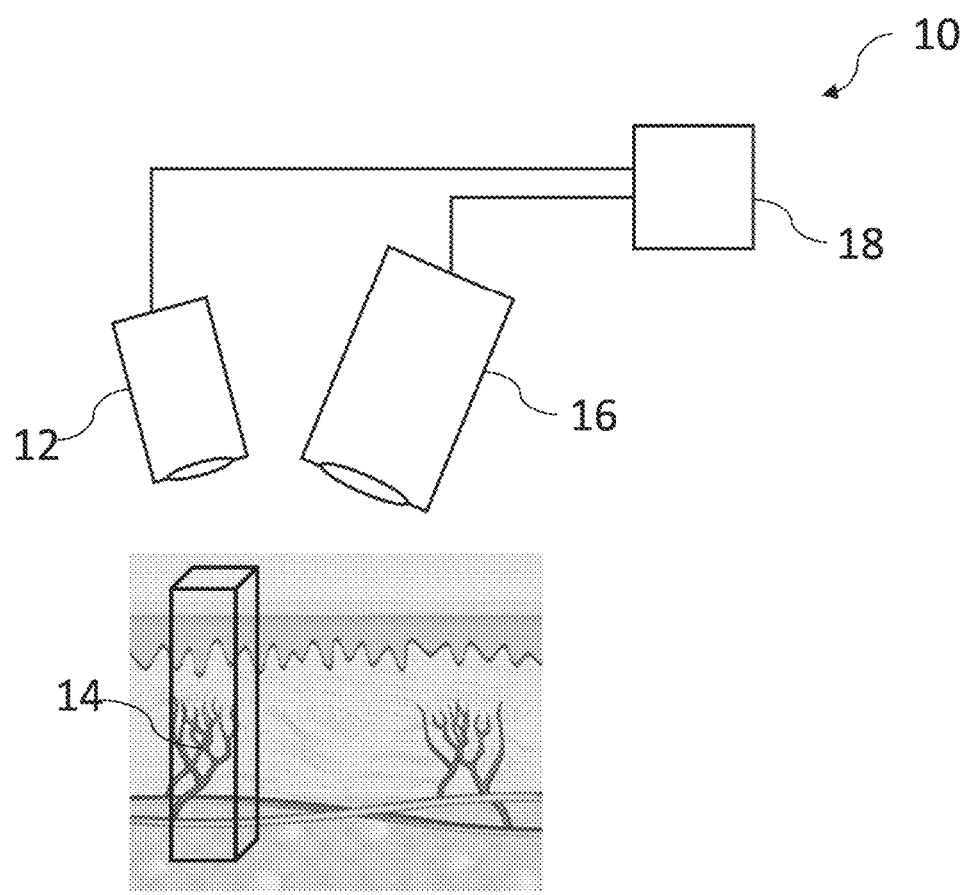
FIG. 6 illustrates an example apparatus for measuring a time-varying change in an amount of blood in a tissue volume according to an embodiment.

Referring to FIG. 6, there is shown schematically an example embodiment of an apparatus 10 for measuring the time-varying change in the amount of blood in the tissue volume. The apparatus 10 comprises a light source 12 configured to excite the fluorescence agent 14 in the blood in the tissue volume, a sensor 16 configured to acquire the time-varying light intensity signal during the pulsatile flow of the blood through the tissue volume, and a processor 18 configured to process the acquired time-varying light intensity signal to provide the measurement of the time-varying change in the amount of blood in the tissue volume.

Figure 7:
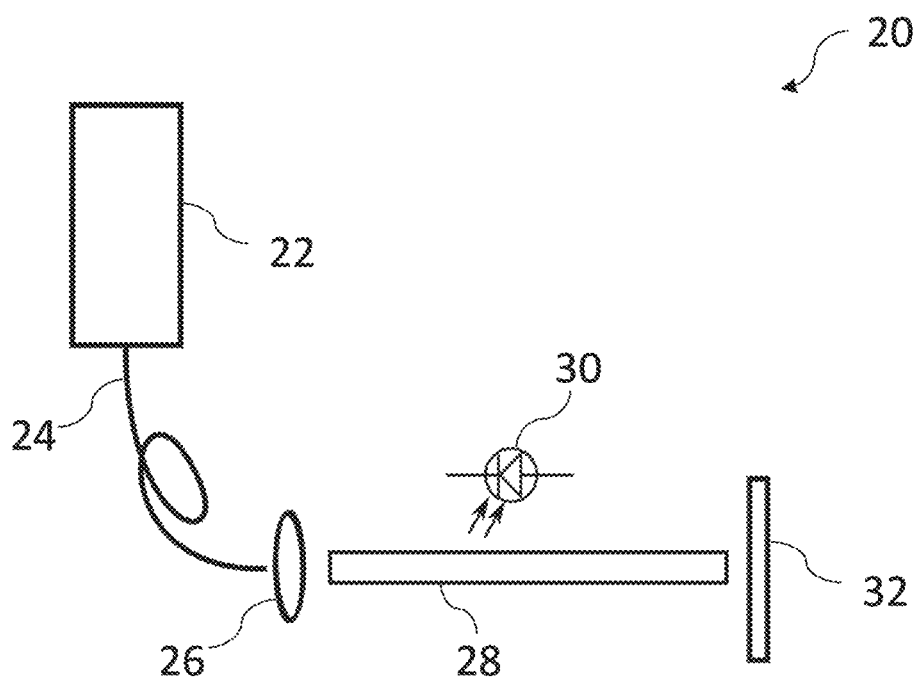
FIG. 7 illustrates an example illumination module according to an embodiment.

In various embodiments, the light source 12 comprises, for example, an illumination module comprising a fluorescence excitation source operatively configured to generate an excitation light having a suitable intensity and a suitable wavelength for exciting the fluorescence agent 14. FIG. 7 shows an example illumination module 20 according to an embodiment. The illumination module 20 comprises a laser diode 22 (e.g., which may comprise, for example, one or more fiber-coupled diode lasers) configured to provide an excitation light to excite the fluorescence agent 14 (not shown). Examples of other sources of the excitation light which may be used in various embodiments include one or more LEDs, arc lamps, or other illuminant technologies of sufficient intensity and appropriate wavelength to excite the fluorescence agent 14 in blood. For example, excitation of the fluorescence agent 14 in blood, wherein the fluorescence agent 14 is a fluorescence dye with near infra-red excitation and emission characteristics, may be performed using one or more 793 nm, conduction-cooled, single bar, fiber-coupled laser diode modules from DILAS Diode Laser Co, Germany.

In various embodiments, the light output from the light source 12 may be projected through an optical element (i.e., one or more optical elements) to shape and guide the output being used to illuminate the tissue area of interest. The shaping optics may consist of one or more lenses, light guides, and/or diffractive elements so as to ensure a flat field over substantially the entire field of view of the fluorescence emission acquisition module. In particular embodiments, the fluorescence excitation source is selected to emit at a wavelength close to the absorption maximum of the fluorescence agent 14 (e.g., a fluorescence dye such as ICG). For example, referring to the embodiment of the illumination module 20 in FIG. 7, the output 24 from the laser diode 22 is passed through one or more focusing lenses 26, and then through a homogenizing light pipe 28 such as, for example, light pipes commonly available from Newport Corporation, USA. Finally, the light is passed through an optical diffractive element 32 (i.e., one or more optical diffusers) such as, for example, ground glass diffractive elements also available from Newport Corporation, USA. Power to the laser diode 22 itself is provided by, for example, a high-current laser driver such as those available from Lumina Power Inc. USA. The laser may be operated in a pulsed mode during the image acquisition process. In this embodiment, an optical sensor such as a solid state photodiode 30 is incorporated into the illumination module 20 and samples the illumination intensity produced by the illumination module 20 via scattered or defuse reflections from the various optical elements. In various embodiments, additional illumination sources may be used to provide guidance when aligning and positioning the module over the area of interest.

Figure 8:
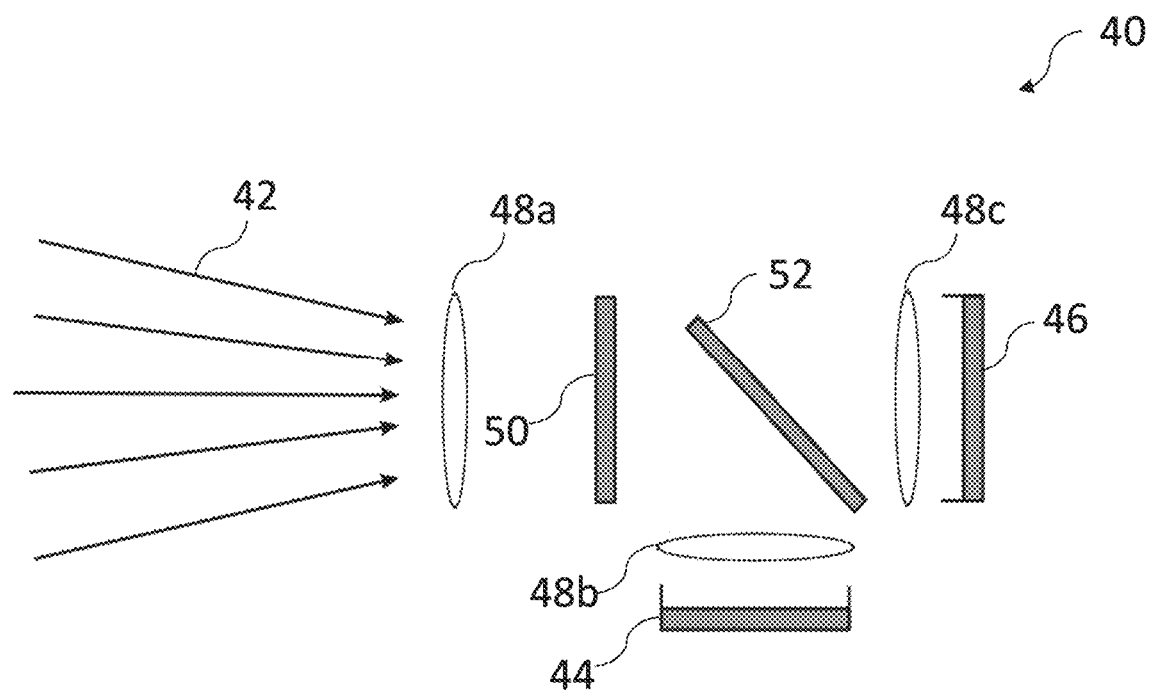
FIG. 8 illustrates an example fluorescence emission acquisition module according to an embodiment.

Referring back to FIG. 6, in various embodiments, the sensor 16 comprises, for example, a fluorescence emission acquisition module configured to acquire a fluorescence signal (e.g., the time-varying light intensity signal) from the fluorescence agent 14, the fluorescence emission acquisition module comprising an image sensor. Referring to FIG. 8, there is shown an exemplary embodiment of a fluorescence emission acquisition module 40 configured to acquire the fluorescence signal such as the time-varying light intensity signal from the fluorescence agent 14 (not shown). As is shown in FIG. 8, the fluorescence emission 42 from the fluorescence agent 14 in blood (not shown) is collected and focused onto a 2D solid state image sensor (e.g. an image sensor 44 and an image sensor 46) using a system of imaging optics 48a, 48b, and 48c. The solid state image sensor may be a charge coupled device (CCD), a CMOS sensor, a CID or similar 2D sensor technology. An optical filter 50 (which may comprise a plurality of optical filters in various arrangements) is used to remove residual and reflected excitation light and to ensure that only the fluorescence emission is recorded at the image sensors 44 and 46. In this embodiment, a dichroic optical filter 52 is used to divide the fluorescence emission spectrum of the fluorescence agent 14 into two spectral channels (e.g., first and second spectral bands). In this embodiment, the dichroic optical filter 52 is designed such that the total fluorescence emission is divided generally equally between the two spectral channels, and such that the shorter wavelength channel collects light of wavelengths equal to or shorter than the fluorescence emission maximum, and the longer wavelength channel collects light equal to or longer than the fluorescence emission maximum. The charge that results from the optical signal transduced by the image sensors 44 and 46 is converted to an electrical video signal, which includes both digital and analog video signals, by the appropriate read-out and amplification electronics in the fluorescence emission acquisition module 40.

Figure 9:
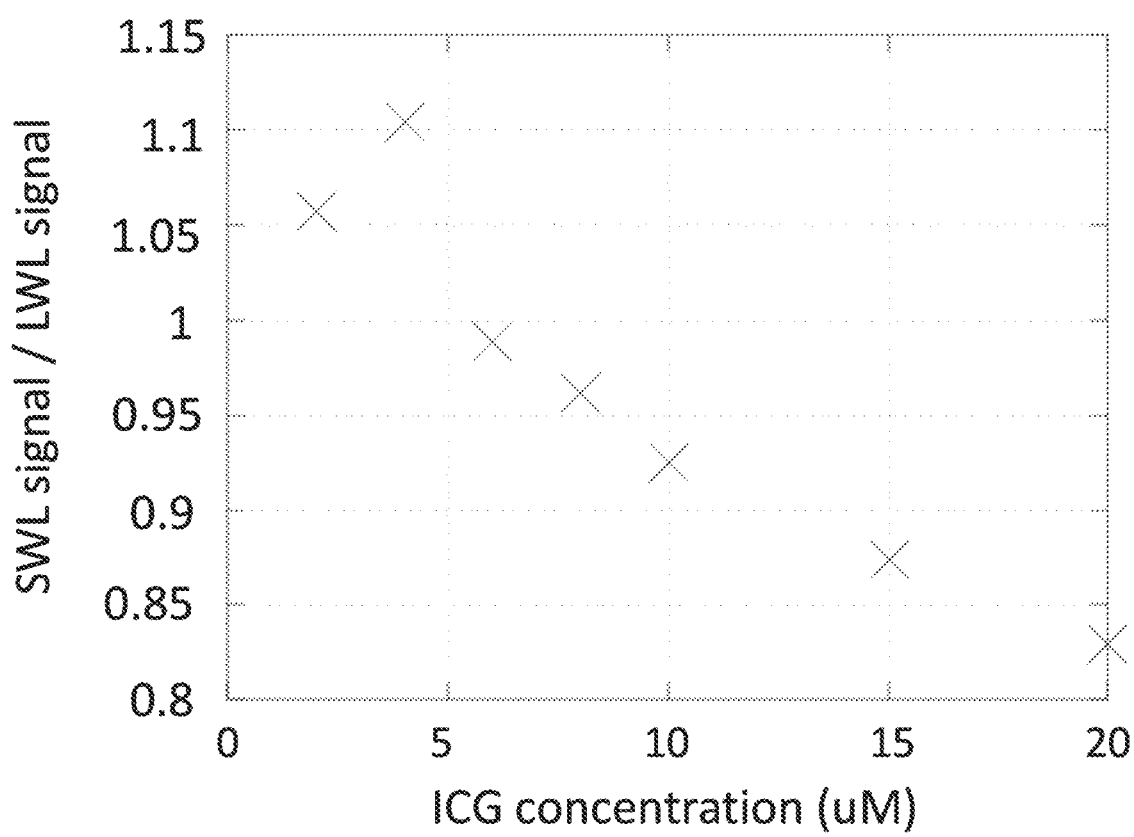
FIG. 9 illustrates an example relationship between a ratio of ICG fluorescence intensities from a first spectral band ranging from about 820 to about 840 nm (where "SWL" denotes a short wavelength) and from the second spectral band ranging from about 840 nm to about 900 nm (where "LWL" denotes a long wavelength) and the instantaneous molar concentration of ICG.

Although only two image sensors 44 and 46 are utilized in the embodiment shown in FIG. 8, the preferred selection of the two spectral bands—where the fluorescence emission over wavelengths in one band monotonically increases with the fluorescence agent concentration and where the fluorescence emission integrated over wavelengths in another band monotonically decreases with the fluorescence agent concentration as shown in FIG. 5 —enables the possibility of utilizing the signals transduced by the two sensors in two beneficial ways. Firstly the signal from the two image sensors 44 and 46 may be combined to obtain the total fluorescence image signal intensity. This will enable the highest quality (lowest noise) fluorescent image to be generated. Secondly, the image signal from these two spectral bands can be ratioed on a pixel by pixel basis to determine the instantaneous molar concentration of fluorescence agent 14 in the blood. The molar concentration is an essential parameter in determining the time-varying change in the amount of blood in the tissue volume. The images from the two image sensors 44 and 46 show identical fields of view on a pixel by pixel basis. Furthermore, the range of variation of the ratio as shown in FIG. 9, is increased and the determination of the instantaneous concentration of the fluorescence agent 14 is consequently more accurate by utilizing the selection of the spectral bands as is described in connection with the various embodiments.

Referring back to FIG. 6, in various embodiments, the processor 18 comprises, for example, a processor module (not shown) configured to analyze time-varying light intensity signals, perform calculations for the plethysmographic computation of the time-varying change in the amount of blood in the tissue volume, output the calculated information to an appropriate display and/or recording device, or a combination thereof. In various embodiments, the processor module comprises any computer or computing means such as, for example, a tablet, laptop, desktop, networked computer, or dedicated standalone microprocessor. Inputs are taken, for example, from the image sensors 44, 46 of the emission acquisition module 40 shown in FIG. 8, from the solid state photodiode 30 in the illumination module 20 in FIG. 7, and from any external control hardware such as a footswitch or remote-control. Output is provided to the laser diode driver, and optical alignment aids. In various embodiments, the processor module may have the capability to save image sequences to internal memory, such as a hard disk or flash memory, so as to enable post-processing of acquired data. In various embodiments, the processor module may have an internal clock to enable control of the various elements and ensure correct timing of illumination and sensor shutters. In various other embodiments, the processor module may also provide user input and graphical display of outputs.

Figure 10:
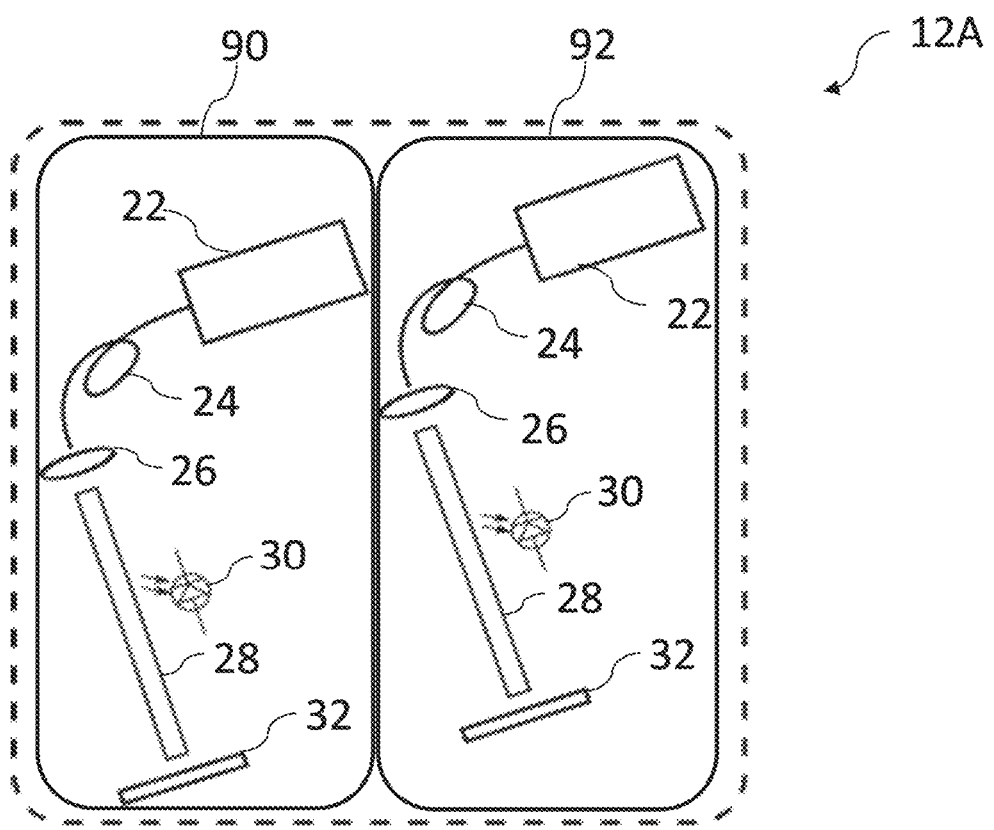
FIG. 10 illustrates an alternative embodiment of the light source of the apparatus in FIG. 6.

In various other embodiments, the apparatus 10 illustrated in FIG. 6, may alternatively comprise the light source 12A configured to excite the fluorescence agent 14 (not shown) as illustrated in FIG. 10. The light source 12A comprises an illumination module comprising a first excitation source 90 and a second excitation source 92 configured to provide an excitation light to excite the fluorescence agent 14 (not shown). The output from each excitation source is passed through beam shaping and smoothing optics as described in connection with the previous embodiments. In this embodiment, the light source (not shown) comprises a fluorescence emission acquisition module consisting of fluorescence collecting and imaging optics similar to those described in connection with the previous embodiments, as well as an optical filter for rejection of residual and reflected excitation light (not shown). This system of optics preferably focuses the collected fluorescence onto a single solid-state image sensor, which is read out by the processing module at each frame.

In operation, and with continuing reference to the embodiments in FIGS. 6 to 8, the subject is positioned such that an area of interest is located beneath both the light source 12, for example comprising the illumination module 20, and the sensor 16, for example comprising the fluorescence emission acquisition module 40, of the apparatus 10, and such that the illumination module 20 produces a substantially uniform field of illumination across substantially the entire area of interest. In various embodiments, prior to the administration of the fluorescence agent 14 to the subject, an image may be acquired of the area of interest for the purposes of background deduction. For example, in order to do this, the operator may initiate the image acquisition procedure by depressing a remote switch or foot-control, or via a keyboard on the processing module (not shown) of the processor 18 of the apparatus 10 in FIG. 6. As a result, the light source 12 (e.g., the laser diode 22 of the illumination module 20 in FIG. 7) is turned on and begins the shutter sequence for the image sensors (e.g., image sensors 44, 46 of the fluorescence emission acquisition module 40 in FIG. 8). When operating in the pulsed mode of the embodiment, each of the image sensors is read out simultaneously with the laser pulses. In this way, maximum fluorescence emission intensity is recorded, and signal-to-noise ratio is optimized. In this embodiment, the fluorescence agent 14 is administered to the subject and delivered to the area of interest via arterial flow. Image acquisition is initiated, for example, shortly after administration of the fluorescence agent 14, and images of the fluorescence returned from substantially the entire area of interest are acquired throughout the ingress of the fluorescence agent 14. The fluorescence emission from the area of interest is collected by the front imaging optics of the fluorescence emission acquisition module 40. Residual and reflected excitation light is attenuated by the optical filters (e.g., optical filter 50 in FIG. 8).

In the embodiment in FIG. 8, the dichroic optical filter 52 is used to divide the total fluorescence acquired into two selected spectral channels, as is described in connection with the various embodiments. In a single exposure, the images recorded by each sensor 44 and 46 are read out and sent to the processor module (not shown) of the processor 18 of the apparatus 10 shown in FIG. 6. In various embodiments, the processor module may perform averaging over adjacent pixels in each frame, as well as over multiple successive frames prior to performing any calculations of perfusion. The images recorded in each of the two spectral channels are compared, and the ratio of fluorescence intensity in each channel is calculated over a kernel of the field of view. The kernel may be a single pixel or an array of pixels in the field of view. Based on the calculated ratio, and on a previous calibration of the apparatus, the concentration of ICG within the kernel is calculated. The combined signal from both image sensors 44 and 46 is then used, together with a measurement of the optical illumination intensity as measured by the sampling solid state photodiode 32 within the illumination module 20 in FIG. 7 to calculate the total fluorescence intensity, and determine the volume of blood in the kernel via an application of the modified Beer-Lambert law as is described in connection with the various embodiments. This processing is repeated over substantially the entire field of view, and the resulting measurement of perfusion (blood flow) is displayed to the user on demand as, for example, a grayscale or false color image, or stored for later analysis.

EXAMPLES

Example #1: Flow Calculation from Volumetric Change

FIGS. 11A to 11C schematically illustrate the individual ICG-filled vessel segments within a rectangular volume of skin tissue, wherein the vessel segments are depicted during pressure pulse diastole (i.e., during a diastolic phase) and during the peak of systole (i.e., during a systolic phase). The arrows in these figures in connection with the tissue volumes (each having a cross-sectional area, A) indicate an increase in ICG fluorescence intensity that occurs when the diameters of the individual blood vessel segments increase as blood pressure rises from the diastolic to the systolic level during the diastolic and systolic phases of cardiovascular pulse, respectively. FIG. 11C schematically replicates the geometrical relationships depicted in FIG. 11B, except that the aggregate volumes of the individual blood vessel segments are represented by a single cubic volume. Additionally, the maximum amount of blood volume increase that occurs between the diastolic and systolic pressures is indicated as $\Delta V$.

The total amount of blood flowing through the rectangular tissue volume during a single pressure pulse oscillation is proportional to the area beneath the pulse curve. If the pressure pulse were a square-wave, then the total volume flowing during a single pulse would be $\Delta V$. However, the pressure pulse curve is not a square-wave, so the area under the actual pulse curve is a fraction of the square-wave area.

Therefore, the pulse duty-cycle ($P_{DC}$) may be defined as the fraction of the area under the square wave occupied by the area under the actual pulse curve. Thus, the actual blood flow through the tissue volume during one pressure pulse cycle, F, is represented by:

$$F=(\Delta V)(P_{DC})/\Delta t, \text{ where}$$

$\Delta V$=(cross-sectional area of the tissue volume end, A)× (thickness increase, $\Delta L$, of the blood volume layer, L), and $\Delta t$=duration of a single pressure pulse, $$\text{therefore, } F=(A)(\Delta L)(P_{DC})/\Delta t \quad (1)$$

Although absolute values can be determined for A, $P_{DC}$, and $\Delta t$, no clinically acceptable method by which to routinely determine $\Delta L$ has previously been demonstrated. Exemplary algorithm embodiments by which $\Delta L$ can be determined quantitatively and from which volumetric change in blood per unit time can be determined are described below.

Example #2: First Method for Fluorescence Agent Concentration Determination

Figure 12A:
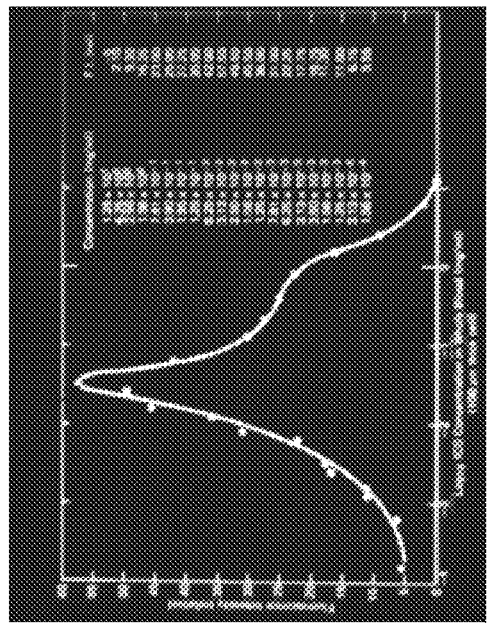
FIGS. 12A and 12B schematically represent the time-varying relationship between ICG concentration and fluorescence intensity during transit of ICG through a blood vessel.
Figure 12B:
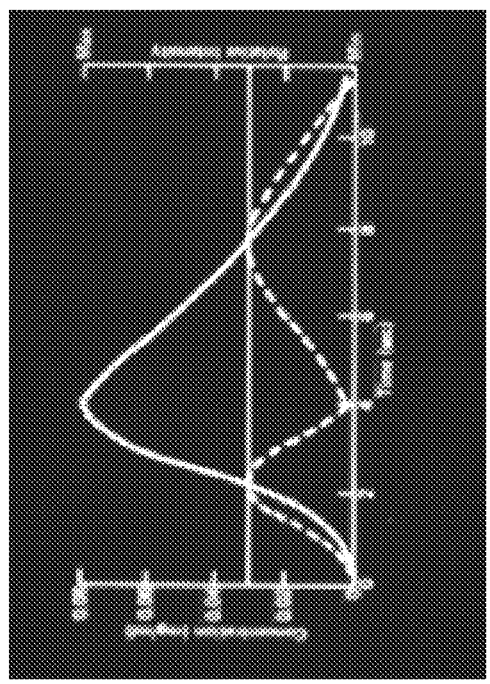

Concentration-dependent fluorescence quenching displayed by a fluorescence dye (e.g. ICG) can be used to determine $\Delta L$ quantitatively in terms of length/time. Concentration-dependent fluorescence quenching is the phenomenon exhibited by certain dyes in solution, wherein the fluorescence intensity emitted by the solution increases along with dye concentration until a point is reached beyond which further concentration increase results in fluorescence diminution. For example, for ICG in blood, maximum fluorescence occurs at a concentration of 0.025 mg/ml (see Flower, R. W. and Hochheimer, B. F.: "Quantification of Indicator Dye Concentration in Ocular Blood Vessels", Exp. Eye Res., Vol. 25: 103, August 1977); above or below this concentration, fluorescence diminution occurs fairly sharply, as shown in FIG. 12A, which schematically illustrates the relationship between ICG concentration and fluorescence intensity of ICG through a blood vessel. FIG. 12B schematically illustrates, for a fixed location within a blood vessel, the time-varying relationship between ICG concentration (solid curve) and fluorescence intensity (dashed curve) during transit of an ICG dye bolus through the vessel.

In particular, FIG. 12A shows the total fluorescence response as a function of increasing ICG concentration, and demonstrates that at high concentration, the agent is self-quenching. FIG. 12B demonstrates, in the solid line, the concentration during transit of a bolus of ICG. In the case of a large, concentrated bolus, the dotted line occurs, which shows the total fluorescence intensity can be quenched nearly to zero during the transit to give a double peaked fluorescence response as a function of time.

FIGS. 12A and 12B indicate the points at which dye concentration is 0.025 mg/ml, and the points at which the concentration is at some significantly greater level at which fluorescence quenching takes place (e.g., in this example, about 10 times greater). FIG. 12B illustrates that as an ICG bolus transits the blood vessel and dye concentration increases (solid curve), ICG fluorescence also increases (dashed line) and reaches a maximum intensity when the dye concentration reaches 0.025 mg/ml (left-hand arrow). As concentration continues to increase, fluorescence decreases due to concentration fluorescence quenching, reaching a minimum intensity (middle arrow) when concentration reaches its maximum (about 0.250 in this example). Thereafter, concentration decreases, causing fluorescence intensity to increase, until it again reaches the maximum level of 0.025 mg/ml (right-hand arrow); then as concentration continues to decrease, fluorescence also begins to decrease again.

The distinctive double peaks of equal maximum fluorescence intensity that occur during transit of an ICG bolus of sufficiently high concentration and volume integrity allow the determination of, in absolute terms, the increase in blood volume thickness, $\Delta L$, depicted in FIG. 11C. Since the peaks occur at a concentration of 0.025 mg/ml, and since the fluorescence intensity emitted from a known area (A) at the precise time either peak occurs can be determined, the thickness of a layer of blood containing 0.025 mg/ml ICG that emits the same fluorescence intensity under identical conditions of illumination and magnification also can be empirically determined.

Figure 13B:
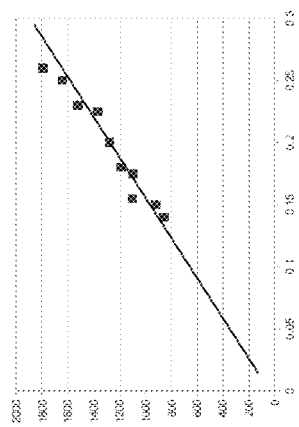
FIGS. 13A and 13B show a fluorescence image of a tapered capillary tube containing a 0.025 mg/ml concentration ICG solution and a graph of the resulting linear relationship between capillary diameter and fluorescence intensity.
Figure 13A:
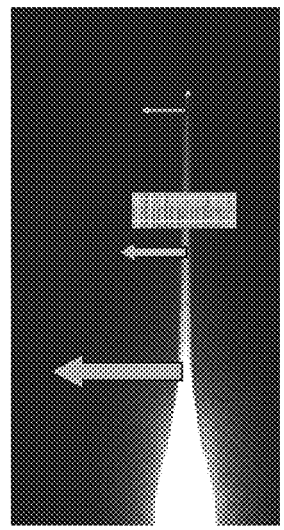

For example, using the same optical device and fluorescence excitation illumination used to acquire the high-speed angiographic images from which the intensity of the double-peaked fluorescence was obtained, a fluorescence image can be obtained of a finely tapered capillary tube filled with a 0.025 mg/ml ICG/blood or ICG/ethanol solution, as is illustrated, for example, in FIG. 13. From this image (FIG. 13A), a graph of the linear relationship between capillary diameter, ΔL, and fluorescence intensity can be generated (FIG. 13B).

Absolute values are now known for all the terms in the equation F=(A×ΔL)/Δt, making it possible to solve for absolute blood flow through the volume of skin tissue lying beneath area A in terms of ml/sec. Therefore, this example illustrates absolute quantification of blood flow in a volume of tissue (e.g., skin blood flow) according to an embodiment.

Figure 14:
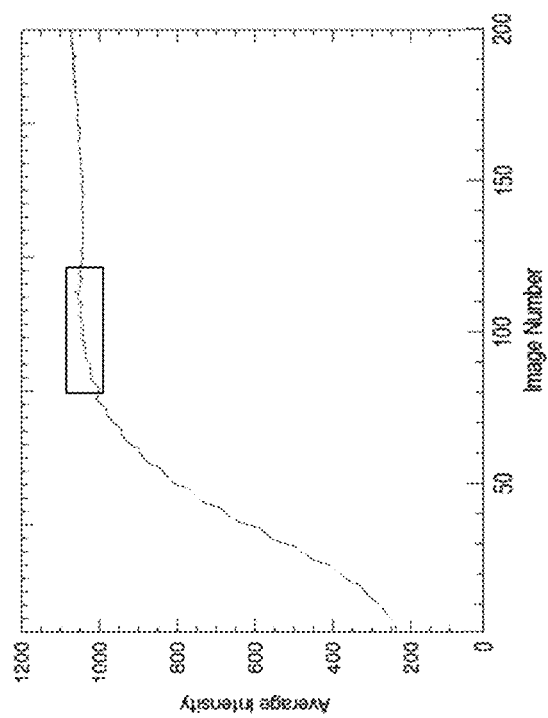
FIG. 14 is a plot of time-varying average fluorescence intensity emitted from an area of human forearm skin following injection of an ICG solution into the cubital vein.

Example #3: Alternate Method for Fluorescence Agent Concentration Determination In another example, following rapid cubital vein injection of 0.40 ml of 50 mg/ml aqueous ICG dye and an immediate, rapid 5.0-ml isotonic saline flush, high-spatial resolution angiographic images of a 250 mm$^2$ area of human medial contralateral forearm skin were obtained at the rate of 23/sec. The individual images in the angiogram sequence were re-registered to remove frame-to-frame arm movement, and from each of these images, average fluorescence intensity for the tissue area was calculated for each image. These data were then used to generate a plot of time-varying average fluorescence intensity, a portion of which (centered approximately about Image Number 100) is shown in FIG. 14.

Figure 15:
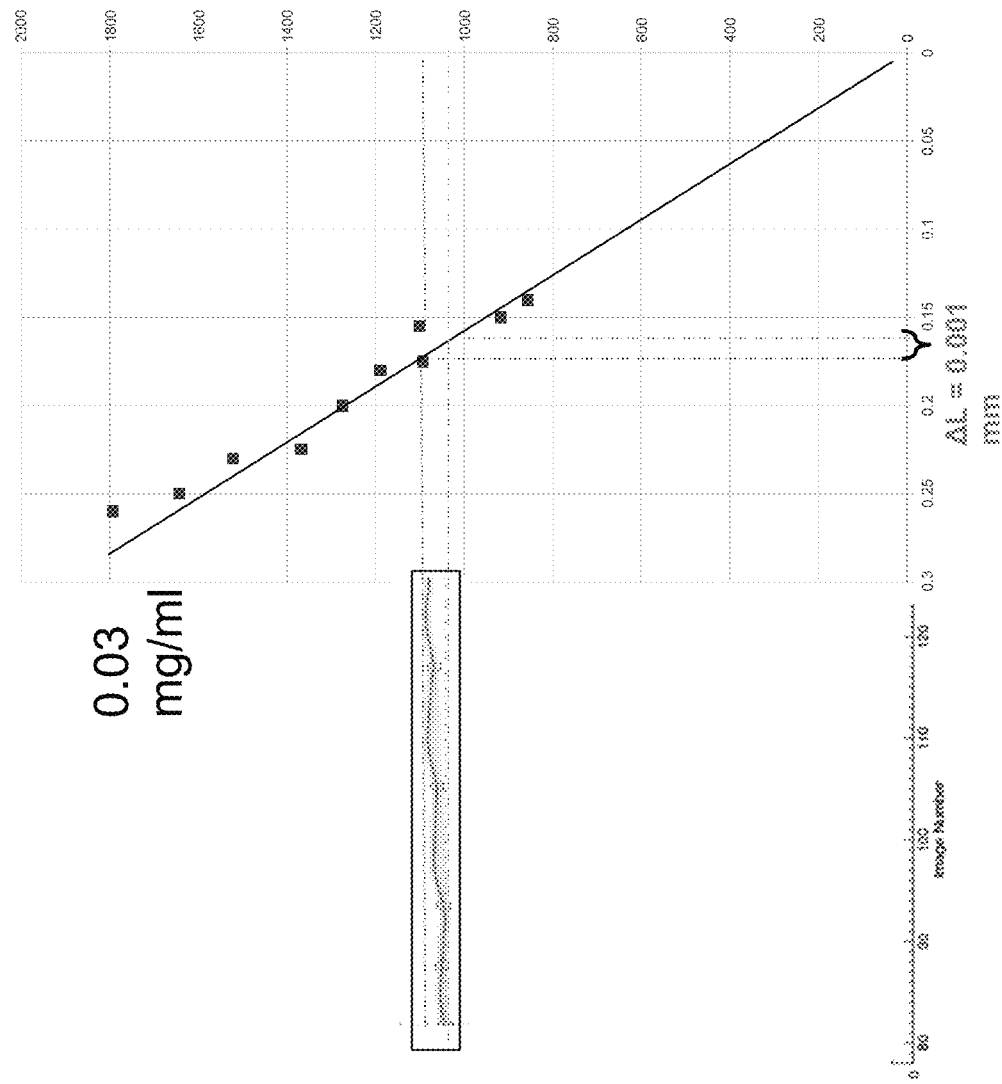
FIG. 15 shows a train of PPG oscillations associated with a plot of fluorescence intensity emitted from a tapered capillary tube containing a 0.03 mg/ml concentration ICG solution as a function of capillary tube thickness.

High-frequency PPG oscillations are clearly visible riding on the low-frequency component of the fluorescence intensity curve which is related to dye filling of the aggregate vascular volume contained within the volume of skin tissue, beneath the 250 mm$^2$ surface area. As is illustrated in FIG. 15, three PPG oscillations (and a fraction of a fourth) centered about image number 100 have been juxtaposed beside a graph of the capillary diameter versus fluorescence data from FIG. 13B. Both graphs are on the same fluorescence intensity scale shown on the right of the figure.

An envelope defined by the minima (dashed line) and maxima (dashed line) of the PPG fluorescence-intensity oscillations is projected onto the fluorescence-intensity versus capillary-diameter graph and then onto the graph's abscissa. The width of the latter projection indicates the thickness of the blood-volume layer increase, ΔL=0.001 mm.

The average pulse duty-cycle ($P_{DC}$) for the three fluorescence-intensity oscillations in this example was determined to be 40%, and the average duration of one pulse was determined to be Δt=0.680 sec.

$$\text{Since } F = (A)(\Delta L)(P_{DC})/\Delta t \quad (1)$$

$$= (250 \text{ mm}^2)(0.001 \text{ mm})(0.40)/(0.680)$$

$$= 0.147 \text{ mm}^3/sec, \text{ or } 0.147 \text{ ml}/sec$$

A very rough approximation can be made using the following average blood circulation and anatomical values:

$$\text{Total cardiac output} = 5 \text{ L/min} = 83.33 \text{ mL}/sec$$

$$\text{Fraction of cardiac output to skin} = 20\% \text{ or } 16.67 \text{ ml}/sec$$

-continued $$\text{Skin area (m}^2) = \{[\text{height (in)} \times \text{weight (lbs)}]/3131\}\ 1/2 =$$

$$\{[68 \times 154]/3131\}\ 1/2 = 1.83 \text{ m}^2 = 1.83 \times 106 \text{ mm}^2$$

Therefore, total blood flow to 1 mm$^2$ of skin =

$$(16.67 \text{ ml}/sec)/(1.83 \times 106) = 9.11 \times 10^{-6} \text{ ml}/sec$$

Hence, blood flow to 250 mm$^2$ of skin =

$$250 \times 9.11 \times 10^{-6} \text{ ml}/sec = 0.0023 \text{ ml}/sec$$

This latter approximation of blood flow to 250 mm$^2$ of skin is about 60-times less than the 0.147 ml/sec derived using the fluorescence-mediated PPG method and system of the present disclosure as illustrated in the example above. However, such a discrepancy in results may be accounted for in view of the inherent assumption that blood flow is uniformly distributed throughout the entire body skin area in the calculation based on circulation/physiologic approximations, and that the capillary-diameter/fluorescence-intensity data in the FM-PPG example were compiled using ICG in ethanol rather than blood and by-eye capillary-diameter measurements were made with a superimposed scale rather than by digital means.

Therefore, this example illustrates that rapid venous injection of a small-volume, high-concentration dye bolus (e.g., ICG), followed by a saline flush to achieve a circulating peak dye concentration in excess of 38-μM, as required in the preceding calibration method, may be suitable for selected clinical implementations.

Example #4: Ratiometric Method for Fluorescence Agent Concentration Determination An alternative calibration method was developed to accommodate the range of peak dye (e.g. ICG) concentrations encountered in routine clinical use. For example, typical ICG administration consists of injecting about 3 ml of 25 mg/ml aqueous solution, followed by a 5 ml saline flush. Injected dye bolus dilution from about 400 to 600 times occurs during intravascular transit to various sites of interest, resulting in a range of peak dye concentration of approximately 5.4- to 8-μM. To accommodate this variability of peak dye concentrations, additional fluorescence wavelength data is acquired simultaneously with the angiographic images; these data are used for dual-wavelength ratiometric analysis for determining intravascular dye concentration at the time each image is acquired.

Whereas the calibration method described earlier has the advantage of requiring no other data except an ICG fluorescence angiography sequence, the alternative calibration method has the advantage of being entirely transparent to the user, in that no deviation from the usual injection technique is required. However, the recording device's imaging optics is modified to permit continuous simultaneous measurement of two near IR wavelengths longer than those used for image formation.

As with the calibration method described earlier, in the alternative calibration method, note that the thickness increase ΔL, of the blood volume layer, L, depicted in FIG. 11C is embedded in the fluorescence generated by illumination of the aggregate ICG-dye tagged blood volume in the rectangular tissue volume during a single pressure pulse oscillation. When the surface area, A, of the rectangular tissue volume is illuminated with 805-nm wavelength laser light, the total fluorescence generated, F, is a function of excitation light intensity, i.e., the ICG molar absorption coefficient at 805-nm, $\epsilon$, the ICG molar concentration, C, the ICG quantum efficiency, $\Phi$, and the aggregated ICG-tagged blood layer thickness, L. That is:

$$F=f(I_e,\epsilon,C,\Phi,L) \quad (2)$$

However, taking into account that the excitation light is absorbed as it travels through ICG tagged blood volume, as described by the Beer-Lambert law of absorption, the intensity of emitted fluorescence light, If, is:

$$If=I_e\Phi(1-e^{-\epsilon CL}) \quad (3)$$

Solving equation (3) for L:

$$L=\ln[I_e\Phi/(I_e\Phi-I_f)](\epsilon C)^{-1} \quad (4),$$

wherein values for all the parameters are known, except for the instantaneous ICG molar concentration, C.

Dye (e.g. ICG) molar concentration can be determined by ratiometric analysis of, for example, two appropriate near-IR wavelengths above the band of wavelengths used to form the dye (e.g. ICG) fluorescence images.

Figure 16:
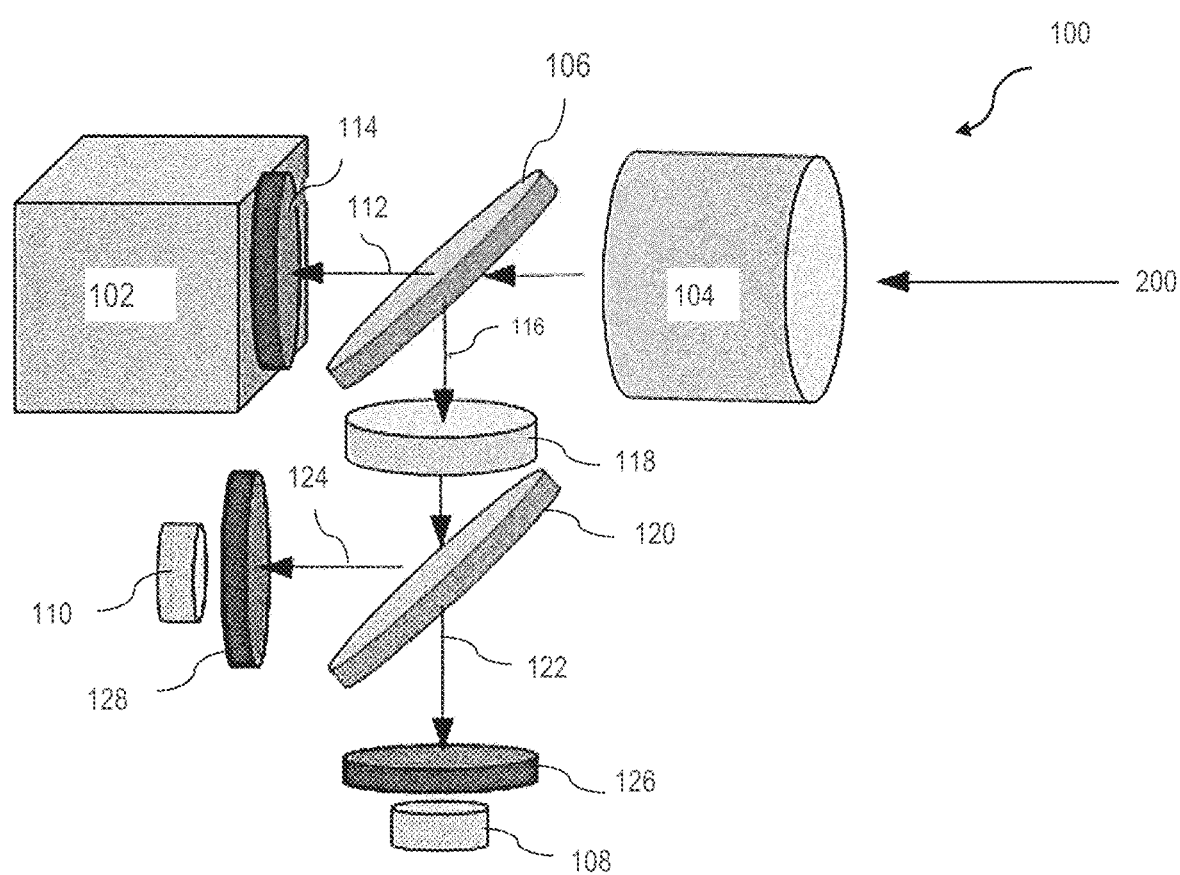
FIG. 16 shows an example imaging system comprising an arrangement of optical components for implementing the FM-PPG methodology according to an embodiment.

Implementation of the ratiometric dye (e.g. ICG) molar concentration determination involves the addition of optical and electronic components into the fluorescence imaging pathway. An example of the insertion of these components, according to an embodiment, is shown schematically in FIG. 16 in the context of the SPY® imaging system by Novadaq Technologies Inc. of Mississauga, Canada. FIG. 16 shows schematically an imaging system 100 which comprises a CCD video camera 102 and an objective lens 104 for fluorescence imaging of fluorescence light from tissue 200. As is shown in the embodiment in FIG. 17, the addition of optical and electronic components (e.g., component 106) into the fluorescence imaging pathway may comprise disposing such components between the SPY® objective lens 104 and the CCD video camera 102. Signal outputs from the two Si photo-detectors 108 and 110 shown in FIG. 16 are real-time analyzed, and the resultant molar concentration determined for each angiographic image will be embedded in its TIFF header and subsequently extracted as needed to determine the instantaneous dye molar concentration in the circulating blood. The embodiment in FIG. 16 is discussed in more detail below in connection with the example of hardware implementation.

The increase in thickness of the blood volume layer, $\Delta L$, that occurs during a pressure pulse can be determined at any time during the angiographic sequence by using equation (4) to determine the layer thickness at the peak of a pressure pulse, $L_p$, and at the pulse minimum, $L_m$, and then calculating the difference between the two:

$$\Delta L=L_p-L_m=\ln[(I_e\Phi-I_m)/(I_e\Phi-I_p)](\epsilon C)^{-1} \quad (5),$$

where $I_p$ and $I_m$ are the respective fluorescence intensities measured at the pulse peak and minimum, and where $L=\ln[I_e\Phi/(I_e\Phi-I_f)](\epsilon C)^{-1}$, wherein, L=aggregate thickness of blood layer in all vessels beneath area A (cm) $I_e$=excitation light intensity (W cm$^{-2}$)
If=intensity of emitted fluorescence light (W cm$^{-2}$)
$\epsilon$=ICG molar absorption coefficient (M$^{-1}$ cm$^{-1}$)
$\Phi$=quantum efficiency (0.13)
A=area of interest (cm$^2$)
C=ICG molar concentration (M)
L is determined at the systolic peak of the blood flow pulse ($L_S$) and at its diastolic minimum ($L_D$), and then flow through the tissue area of interest (A) is calculated as:

Flow=A($L_S$–$L_D$)/time, and wherein, time is reckoned as the duration of the blood flow pulse.

The fluorescence intensities $I_p$ and $I_m$ may be determined, for example, using the same data used in the example algorithm depicted in FIG. 15, wherein the average intensity levels forming an envelope about the pressure pulses from the angiogram images in the shaded area in FIG. 14 are represented by the dashed horizontal lines. In the present example, however, those two horizontal are projected to the relative fluorescence intensity scale on the right-hand side of the graph; one line intercepts the ordinate at 1100, and the other line intercepts at 1035.

In order to convert these relative intensity levels for $I_p$ and $I_m$ to actual light intensity levels ($\mu$W/cm$^2$), the CCD video camera was used as a light meter by calibrating the camera's gray scale output against controlled dye (e.g., ICG) fluorescence intensity input levels.

The calibration method was devised to take into account that the total fluorescence ($I_f$, equation 3) is emitted spherically, and that only a fraction of it is detected by the camera, dependent upon the aperture diameter of the imaging system and the distance of the aperture from the emitting source. The camera's output was found to be linear from approximately 50- to 2500-$\mu$W, such that:

$$I_f(\mu W)=(\text{avg. intensity}-100)/413.012 \quad (6),$$

therefore, $I_p$=2.905 $\mu$W, and $I_m$=2.749 $\mu$W.

Noting that during acquisition of the angiogram data depicted in FIG. 11, $I_e$=4.0 W, equation (5) becomes: $\Delta L$=ln [((4000×10$^{-3}$×0.13)−(2.749×10−3))/((4000×10−3×0.13)−(2.905×10$^{-1}$))]($\epsilon C$)$^{-1}$=0.0005 mm Inserting this value for $\Delta L$ into equation (1): $F =$ $(A)(\Delta L)(P_{DC})/\Delta t = (250 \text{ mm}^2)(0.0005 \text{ mm})(0.40)/(0.680) =$ 0.0735 mm$^3$/sec, or 0.0735 ml/sec This blood flow (0.0735 ml/sec) is half that calculated by the previous method (0.147 ml/sec) used in the first example, making it closer to the approximation of 0.0023 ml/sec that was based on whole-body physiological parameters.

Variations in skin blood flow are induced by changes in a number of physiological parameters, as well as by changes in ambient temperature. To determine the magnitude of such variations, an experiment was performed in which two ICG angiograms of the same 250 mm$^2$ area of human forearm skin as in the example above were recorded within a period of 32 minutes, each following rapid injection of 0.33 ml of 25 mg/ml ICG and a 5 ml saline flush into the contralateral cubicle vein. The first angiogram was recorded at an ambient room temperature of about 70° F., and the second was recorded immediately after exposure for about 1 minute to radiation from a 24 W quartz halogen lamp at a distance of 6 inches; the temperature sensation was similar to that produced by rapid exhalation of breath through the mouth at a distance of several inches.

Figure 17:
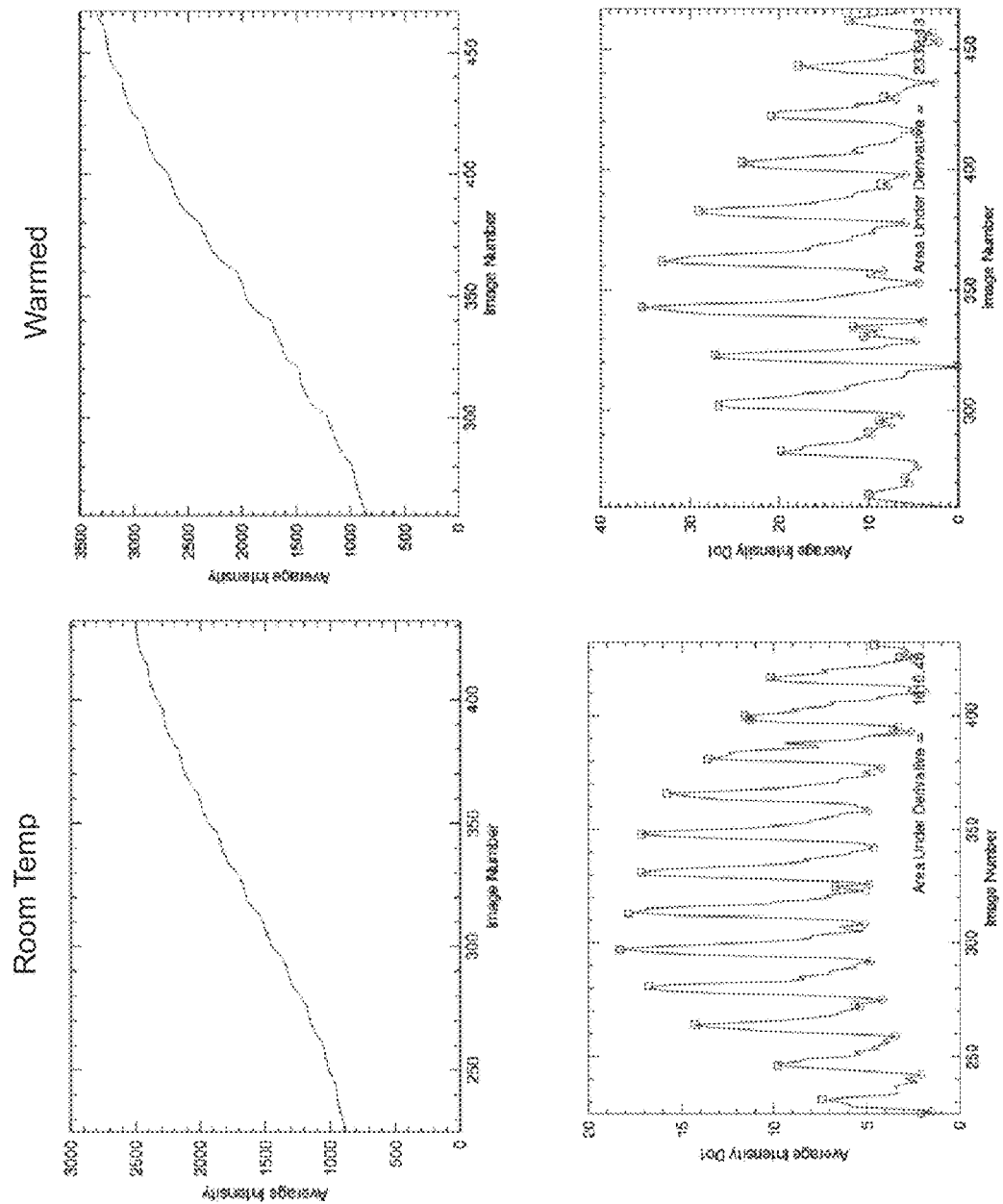
FIG. 17 displays segments of time-varying average intensity graphs from certain working examples of the present disclosure contained herein.

FIG. 17 shows segments of the time-varying average intensity graphs from the two experiments (top row) along with their respective first-derivative with respect to time graphs (bottom row). Since this experiment was performed prior to implementation of the calibration part of the FM-PPG algorithm, the calculated skin area blood flows at the bottom of the figure are only in relative terms, rather than the absolute terms of ml/sec. Nevertheless, the fact that blood flow was about 1.4 times greater at slightly elevated temperature, compared to ambient room temperature, is an indication of the range of variability in normal skin tissue that might be expected in FM-PPG blood flow measurements unless temperature and other physiological parameters at the time of data collection are not taken into account.

In this example, ICG was administered intravenously to a subject by injecting an ICG dye bolus of sufficiently high concentration that, during transit through the tissue site of interest, peak dye concentration would exceed 0.025 mg/ml (the maximum fluorescence intensity, and where concentration fluorescence quenching starts as described in more detail below). Under those conditions, the sub-sequence of angiogram images recording dye transit contained the information needed to determine ICG molar concentration for each image in the entire sequence as a function of image gray-scale intensity, assuming dye excitation level was constant throughout angiogram recording and that fluorescence-intensity vs. CCD camera gray-scale-output is known.

To counteract ICG dye fluorescence quenching, a real-time, two-wavelength ratiometric method for determination of ICG molar concentration in circulating blood was developed. It involves no special preparation, no deviation from a practitioner's usual regimen for dye injection, nor that the transit-phase of dye through the tissue of interest necessarily be recorded, but that fluorescence excitation intensity be maintained at a known constant level during image acquisition and that angiography not be performed when circulating blood is dye-saturated or that significant vascular staining has occurred. In various embodiments, implementation of the wavelength-ratiometric method involves additional optics and hardware and software for determining, simultaneously with each image acquired, the intensities of two bands of near-IR-wavelengths and for embedding these data in the corresponding image header. So far as angiogram acquisition is concerned, these additions and events are entirely transparent to the operator of any device incorporating them. In various embodiments, additional calibration steps are carried out on each device prior to its entering routine clinical use.

To evaluate the ratiometric method of ICG molar concentration, the ICG fluorescence imaging optical path of a FM-PPG system such as, for example, the imaging system 100 shown in FIG. 16, was modified by insertion of a beam-splitter 106 between the objective lens 104 and CCD video camera 102 as is illustrated in FIG. 16. In this example, the beam splitter 106 transmitted the band of ICG fluorescence wavelength(s) 112 used for image capture (approximately 815 to 845 nm wavelengths, which may be filtered by a bandpass filter 114) and diverted all higher wavelength(s) 116 (e.g., wavelengths>845 nm) to a parallel path (which may include a relay lens 118), along which the light was further divided by a second beam-splitter 120 into wavelengths less than approximately 875 nm (wavelength(s) 122) and wavelengths greater than approximately 875 nm (wavelength(s) 124). At the ends of these latter pathways were placed near-IR sensitive Si detectors (e.g, Si detectors 108 and 110) (Thorlabs, model PDA36A Si Switchable Gain Detector). Initially, narrow band-width filters centered about 850 (filter 126) and 900 nm (filter 128), respectively, were inserted in front of each of the detectors 108 and 110 to approximate the front-face-excitation fluorescence emission spectral data from whole blood samples containing 2-, 4-, 8-, 16-, and 32-μM ICG used to determine the two wavelengths on which the ratiometric method was based. A subsequent analysis indicated that in another variation, substantially the same ratiometric discrimination could be made using much wider bandwidths. Accordingly, in this embodiment, the narrow band-width filters were removed, thereby increasing the light intensity impinging on the Si detectors. It is noteworthy that the light impinging on each Si detector is reckoned to arise from the entire field of view recorded in each angiogram image. However, due to analysis equipment availability limitations, the post-secondary-beam-splitter light paths and focusing of light onto the Si detectors has not been rigorously verified.

In this example, each Si-detector amplifier output was connected to one of two input channels of a high-resolution digitizer (Advantech 10M, 12 bit, 4 ch Simultaneous Analog Input Card, Model PCI-1714UL-BE), and the trigger output from the CCD video camera was connected to the digitizer's trigger input channel. Digitized outputs from each channel were inserted by the custom λ-link software into the header of each angiogram image recorded. The digitizer continuously acquired an aggregate of 500 k data samples per second, derived cyclically in equal portions from each of the three input channels. When custom λ-link software detected a rise above the 1.5-volt threshold in the camera trigger channel (signifying onset of a 5-msec pulse of excitation light from the 805-nm laser), data sample counting and recording from the other two channels started. The first 300 samples from the 850-nm channel were excluded (to avoid artifact associated with laser pulse rise time), the next 600 samples were recorded (empirically determined to be the optimal amount), and rest were excluded; the same acquisition algorithm was then applied to samples from the 900-nm channel. When the trigger channel voltage dropped below 1.5 volts at the end of the laser pulse, the program was primed to look for the next voltage rise above the threshold level.

The analysis part of the λ-link software was constructed that in the Phi-motion mode, intensity data from the 850- and 900-nm wavelength bands of light simultaneously embedded in each recorded angiogram image were extracted, producing two streams of digital voltage from the Si detector amplifiers. Each stream contained 600 data samples per excitation laser pulse (i.e., per image), so a total of 1,200 data samples were stored in each image header. The average level of the voltage samples from the 850-nm channel was divided by the average level of the samples from the 900-nm channel, producing a ratio that is transformed (via the calibration curve) into a μM-concentration of ICG (C) used to calculate absolute tissue perfusion.

The digitized outputs from the two channels, as well as the 2-wavelength ratio, were reported to 6 decimal places. It was empirically determined that the rolling average ratio from 40 consecutive images (the number recorded in approximately 1.7 seconds) was stable to 3 decimal places; therefore the last three are truncated for purposes of calculation and reporting.

The calibration curve associated with the example system is unique to the particular combination of parameters related to both its electrical and optical components (e.g., lens aperture, excitation laser power, Si-detector amplification, etc.), many of which have been optimized by empirical experimentation. Necessary characteristics of the curve are that it is monotonic, has a slope (positive or negative) sufficiently steep to permit adequate resolution for determining ICG concentration in blood, is reproducible for the given fixed set of device parameters, and is essentially independent of sample thickness.

Construction of the calibration curve for the system was based on samples of freshly acquired anticoagulated whole human blood containing 2-, 4-, 8-, 12, and 16-μM concentrations of freshly reconstituted ICG dye. Three milliliters of each sample was placed in an open-top Petri dish, producing a 1.764-mm thick layer of blood with a large enough surface area to completely fill the device's field of view.

One by one, each of the five samples was positioned under the objective lens 104 of the imaging system 100, and a sequence of angiographic images approximately 5-sec long was recorded; this procedure was repeated twice more, as quickly as possible to avoid settling of the erythrocytes suspended in plasma. One-half milliliter of blood was removed from each sample, reducing the blood layer thickness by 0.294 mm, and again three sets of angiographic sequences of the five samples were recorded. Then an additional 0.5 ml of blood was removed from each sample, and the final three sets of angiographic sequences were recorded. Thus, nine sets of ratiometric data were acquired from each of the five ICG/blood samples, three sets each from three different sample thicknesses.

For purposes of comparison, identical sequences of ratiometric data were acquired from five samples of ICG in ethanol having a range of ICG concentrations identical to that of the ICG/blood samples. In this case, however, only one angiographic sequence instead of three was recorded from each of the five samples per sample layer thickness. This deviation from the ICG/blood protocol was necessitated by the fact that absorption of excitation light energy, especially with the higher ICG concentration samples, accelerated ethanol evaporation, thereby reducing sample layer thickness, as well as increasing sample concentration.

Figure 18:
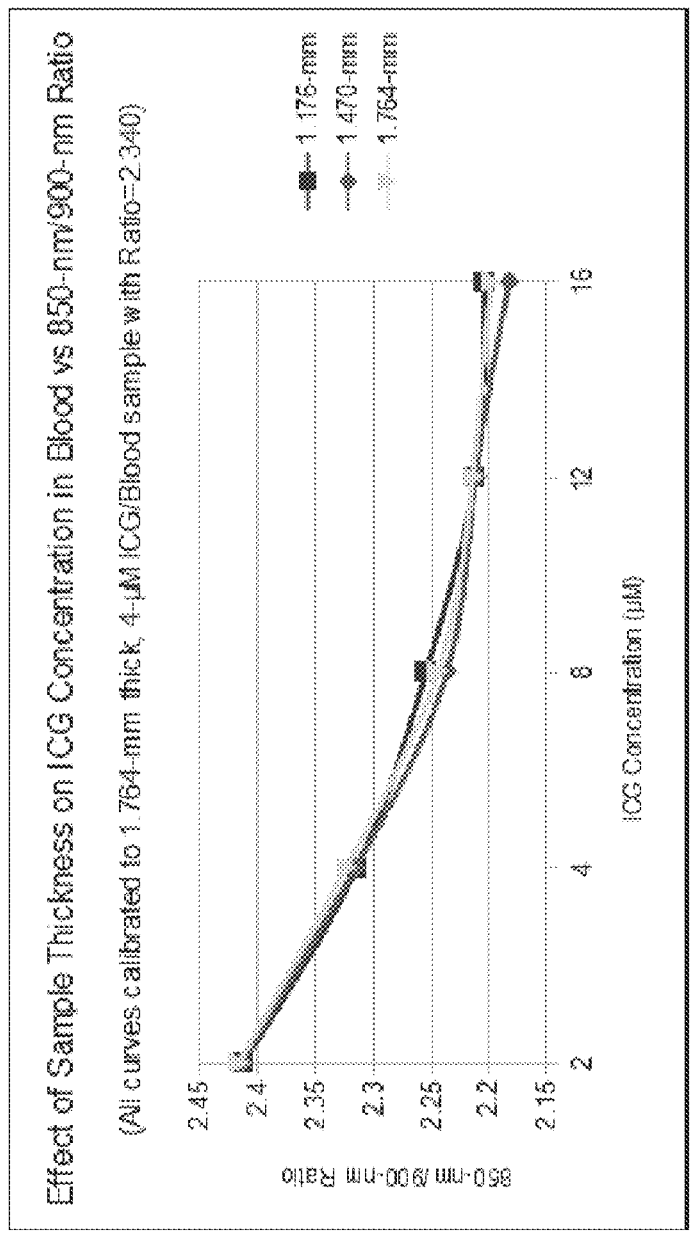
FIG. 18 illustrates the effect of sample thickness on the example ratiometric calibration curves constructed for ICG in ethanol.
Figure 19:
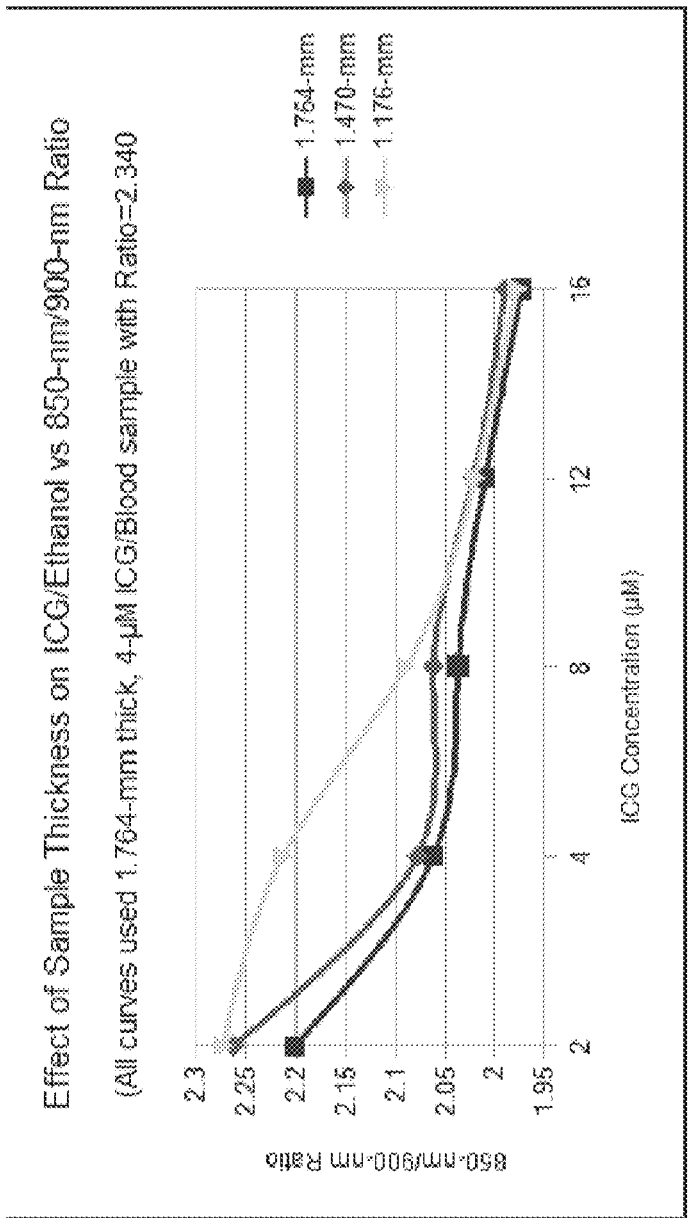
FIG. 19 illustrates the effect of sample thickness on the example ratiometric calibration curves constructed for ICG in human blood.

FIGS. 18 and 19 illustrate the effect of sample thickness on the 2-wavelength ratiometric calibration curves constructed for ICG in ethanol and in human blood, respectively. Although solutions of ICG in whole blood, serum, and ethanol exhibit similar behavior in terms of emitted fluorescence intensity as a function of ICG concentration, the curves in FIGS. 18 and 19 illustrate significantly different behavior between blood and ethanol solutions, especially at lower dye concentrations, in terms of the relationships between intensities of the bands of emitted wavelengths used to construct the 2-wavelength ratiometric calibration curves. A breakdown of the Beer-Lambert law related to differences in chemical interactions (e.g., dissociation and interaction) between ICG and the two solutes may account for this difference. The empirically derived calibration curve for ICG in blood meets the currently understood requisite characteristics as described above in this specification.

Figure 20:
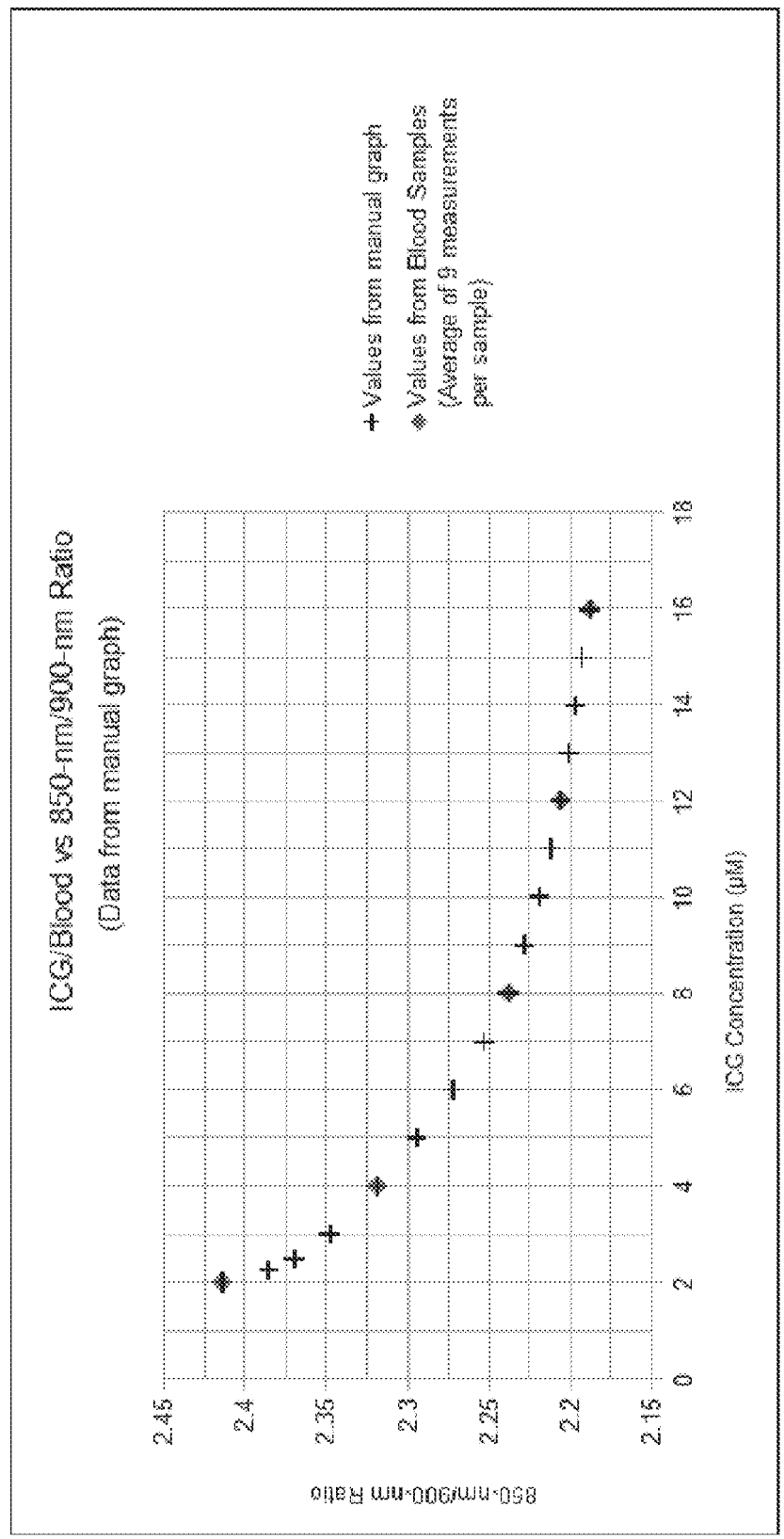
FIG. 20 illustrates a calibration curve interpolated from five data points.

To use the calibration curve in conjunction with the software-embedded algorithm that calculates tissue perfusion, it has to be accessible in a digital format and appear to the software as a continuous function, even though, in this example, it is constructed from only five data points. This may be accomplished by finding an equation describing a smooth curve that passes through all five points. Unfortunately, no linear or second-order polynomial was found that fit satisfactorily, so a graph was manually constructed that does pass through all five points; and from it, twelve additional data points were derived, resulting in the curve in FIG. 20. The software program interpolates between the total of 17 data points. The calibration curve is shown in FIG. 20. As is shown in FIG. 21, average variability of the ratio data along the curve averages +/−0.014.

Generation of the fluorescence data from human blood containing various concentrations of ICG used to determine the optimal wavelengths for construction of the ratiometric calibration curve was commissioned to the Berezin Laboratory at Washington University School of Medicine (St. Louis, Mo.). Berezin Lab was one of a few facilities with an available spectrofluorometer having a spectral range far enough into the near-IR region to produce high-resolution data needed to confirm the original data, upon which the 2-wavelength ratiometric method and system were based.

It is expected that the two calibration curves will be different in terms of noise level and resolution, because the Berezin device effectively has a single optical pathway (channel) and uses the same detector to acquire all wavelength data, whereas the prototype system has two separate pathways and uses two different detectors, as well as two different signal amplifiers, etc. Both devices are capable of producing calibration curves that meet the minimum characteristics as described above in this specification, even if the curves look different.

Figure 21:
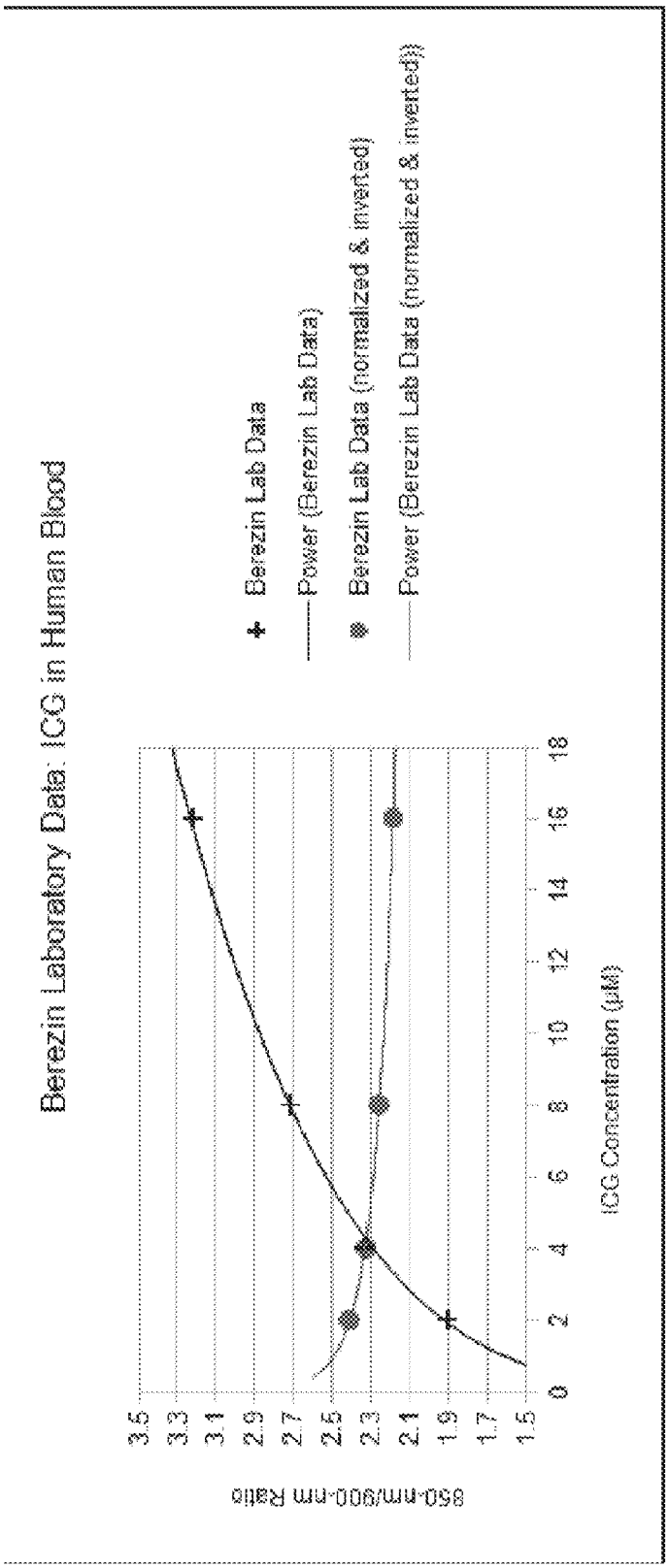
FIG. 21 illustrates data for ICG in human blood.
Figure 22:
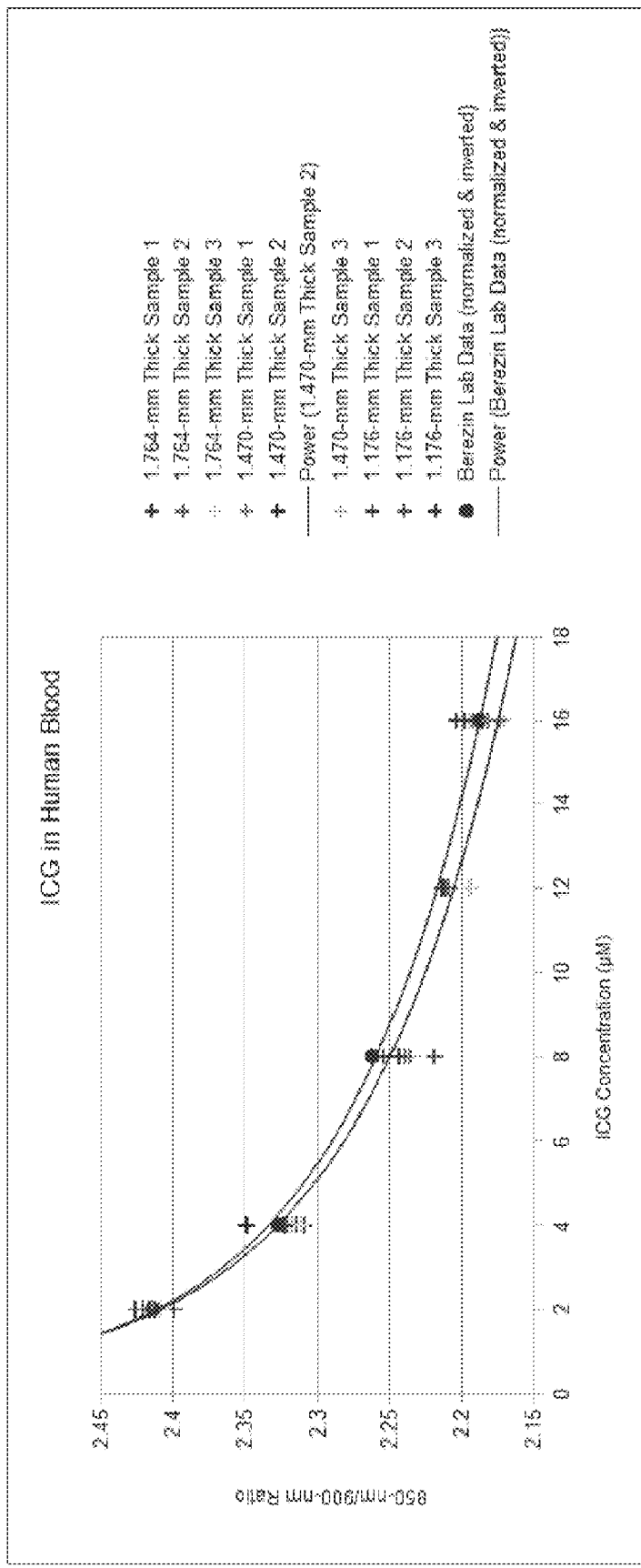
FIG. 22 shows a comparison of the data generated using the FM-PPG example method and system from FIG. 14 with data for ICG in human blood.

As comparison of the curve in FIG. 20 and the curve in FIG. 21 (with crosses as data points) demonstrate, they are quite different: although both are monotonic, their slopes are opposite, and the ratio range of the Berezin data is about five times greater. But neither of these invalidates the curve from the experimental system. In fact, by normalizing the ratio scale of the Berezin curve to that of the experimental system (which offsets differences associated with signal intensity and amplification) and by changing the direction of the Berezin data ratio scale (flipping the curve, thereby changing its slope), the resulting curve in FIG. 22 (with circles as data points) closely matches that of the prototype system, as illustrated in FIG. 22.

The transform function used to normalize the Berezin data ratio scale was as follows:

$$R_1 = (R_0/5.796) + 1.858$$

where:
$R_0$ is the original data point value on the Berezin Ratio scale;
$R_1$ is the transformed point value to be plotted on the prototype device Ratio scale;
5.796 is how much larger the Berezin Ratio data range (difference between the 2- and 16-µM Ratio values) and that for the prototype device; and 1.858 is the amount by which R1 for the 16-µM Berezin sample was shifted on the experimental device's scale (after the Berezin curve was flipped) in order to make it correspond to the location of the experimental device's 2-µM data point.

The computer-generated second-order polynomial curve (labeled "Power") for the prototype system data does not fit well; this is underscored by the skewness with which it pass through the spread of "+" data points for both the 8- or 16-µM concentrations. Nevertheless, significantly the transformed and flipped "Power" curve for the Berezin data lies entirely within the average-variability envelope of the prototype device's "Power" curve, as delineated by the spreads of data points. This demonstrates that the absolute values of the inter-point relationships for both the Berezin and experimental device data are essentially the same. Therefore, by the best measure currently available, the hard- and soft-ware for determination of ICG concentration in blood appear to be optimized and adequate for human subject evaluation.

Example #5: Comparison of FM-PPG with Radio-Labeled Microspheres

Due to a dearth of published data regarding absolute blood flow levels through various tissues, validation of the tissue perfusion analysis program is difficult beyond rudimentary bench-top experiments. There being no available data regarding readily accessible tissue for comparison, proof-of-concept of the algorithm and experimental device in living tissue heretofore has been in connection with analysis of angiogram data acquired from the medial forearm.

The only blood flow data rendered in absolute terms from tissue accessible without invasive procedures that might serve as a gold standard for comparison was derived from rhesus monkey ocular tissues by Alm and Bill (Exp. Eye Res. 15: 15-29, 1973). These data were derived from, using the well-established method of radiolabeled microsphere injection, are rendered in terms of mg/min/mm$^2$. Conversion of their data to µL/sec/mm$^2$ requires knowing only that the average density of blood is 1.06×103 kg/m$^3$, the following relationship is easily derived:

$$X(mg/min/mm^2)/63.6=X(\mu L/sec/mm^2)$$

For example, for acquisition of angiographic data from ocular tissue, a fundus camera may be used. However, a fundus camera has no provision for simultaneous acquisition of the additional two wavelengths of data needed for ratiometric determination of the concentration of ICG in circulating blood (C). However, there are alternative ways to determine when during the transit of an ICG bolus, a concentration of 32.2 µM was reached, and a short sequence of images recorded at that time could be analyzed by the FM-PPG algorithm, the results of which can be compared to that of Alm and Bill.

One alternative method is based on concentration fluorescence quenching, a phenomenon exhibited by ICG dye in solution, wherein the fluorescence intensity emitted by the solution increases along with dye concentration until a point is reached beyond which further concentration increase results in fluorescence diminution. For ICG in blood, maximum fluorescence occurs at a concentration of 0.025 mg/ml; above or below this concentration, fluorescence diminution occurs fairly sharply. As an injected ICG bolus transits a network of blood vessels and dye concentration increases, ICG fluorescence also increases and reaches a maximum intensity when the dye concentration reaches 0.025 mg/ml. As concentration continues to increase, fluorescence decreases due to concentration fluorescence quenching, reaching a minimum intensity when concentration reaches its maximum. Thereafter, concentration decreases, causing fluorescence intensity to increase, until it again reaches the maximum level of 0.025 mg/ml; then as concentration continues to decrease, fluorescence also begins to decrease again. Thus, in a plot of overall image brightness versus image number for a sequence of ICG fundus angiograms in which quenching occurred would contain distinctive double peaks of equal fluorescence intensity. Such quenching can be induced in the ocular vasculatures by injecting an ICG bolus of sufficiently high concentration and volume integrity, but only if the dye injection and an immediately following saline flush of proper volume are made rapidly.

A second alternative is based on previously determined amounts of dilution that cubital vein injected dye boluses undergo during transit to the ocular blood vessels (Invest. Ophthal. 12:881-895, 1973): 310 times in an average adult rhesus monkey, and 600 times in an average adult human. Again, a plot of overall image brightness versus image number for a sequence of ICG fundus angiograms can be used, this time simply to determine the subset of angiogram images that were acquired during peak brightness. The peak brightness is then associated with an ICG concentration 1/600 (in human) or 1/310 (in rhesus) that of the injected dye bolus concentration.

In this example, the subject is the dilated right eye of an anesthetized 8.79-kg rhesus monkey (nearly identical to cynomolgus monkeys). Three angiographic sequences were recorded, as follows:

Sequence 1—saphenous vein injection of 0.1 ml (25 mg/0.7 ml ICG solution) followed immediately by a rapid 3.0 ml saline flush.

Sequence 2—3.0 minutes later with no additional dye injection

Sequence 3—3.0 minutes later, saphenous vein injection of 0.1 ml (25 mg/0.5 ml ICG solution) followed immediately by a rapid 3.0 ml saline flush.

Figure 23:
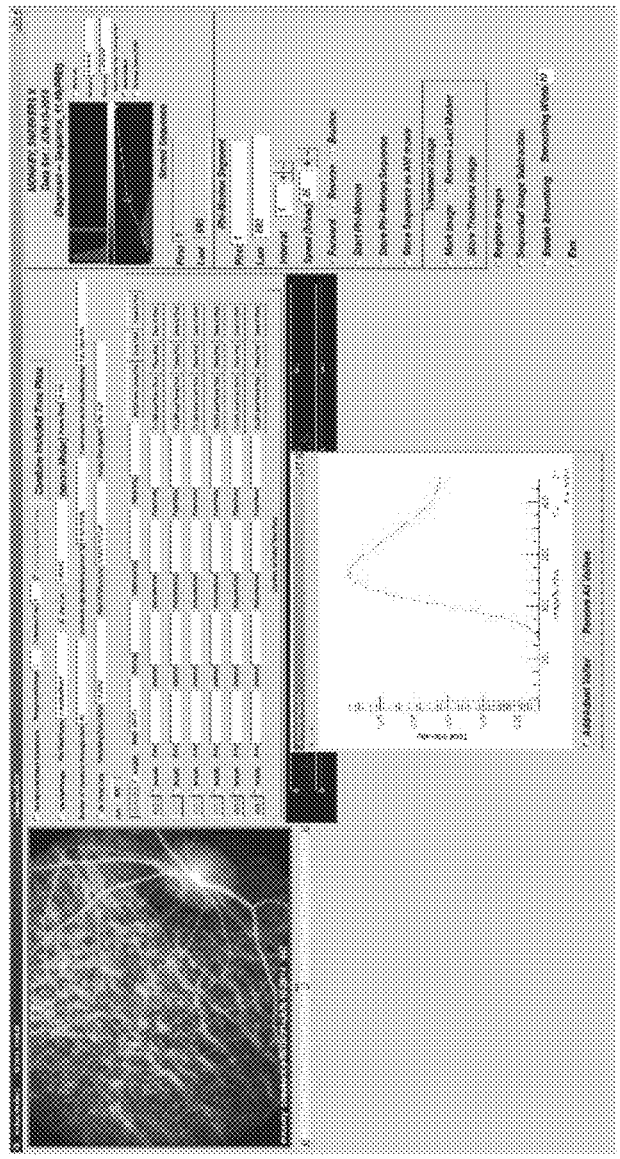
FIG. 23 shows FM-PPG data from a Rhesus monkey eye, and in particular, for analysis of each sequence a time plot of image brightness (total intensity) vs. image number.

For analysis of each sequence, a Time Plot of image brightness (Total Intensity) versus image number was constructed for the first sequence, as shown in FIG. 23. From that plot, it was determined the subsequence of images 490-565 were at peak brightness. Since no double peak was detected, the second alternative method for determining the concentration of ICG in circulating blood, as previously described above, was used. That is, the concentration of the first ICG bolus injected was 25 mg/0.7 ml=35.7 mg/ml, which was diluted by 310 times, to a concentration of 0.115 mg/ml during its transit to the eye. Therefore, the peak concentration of dye in the ocular vessels (corresponding to images 490-565) was 148 µM; that value was entered into the appropriate box on the analysis window in lieu of having 2-wavelength ratiometric data available.

Figure 24:
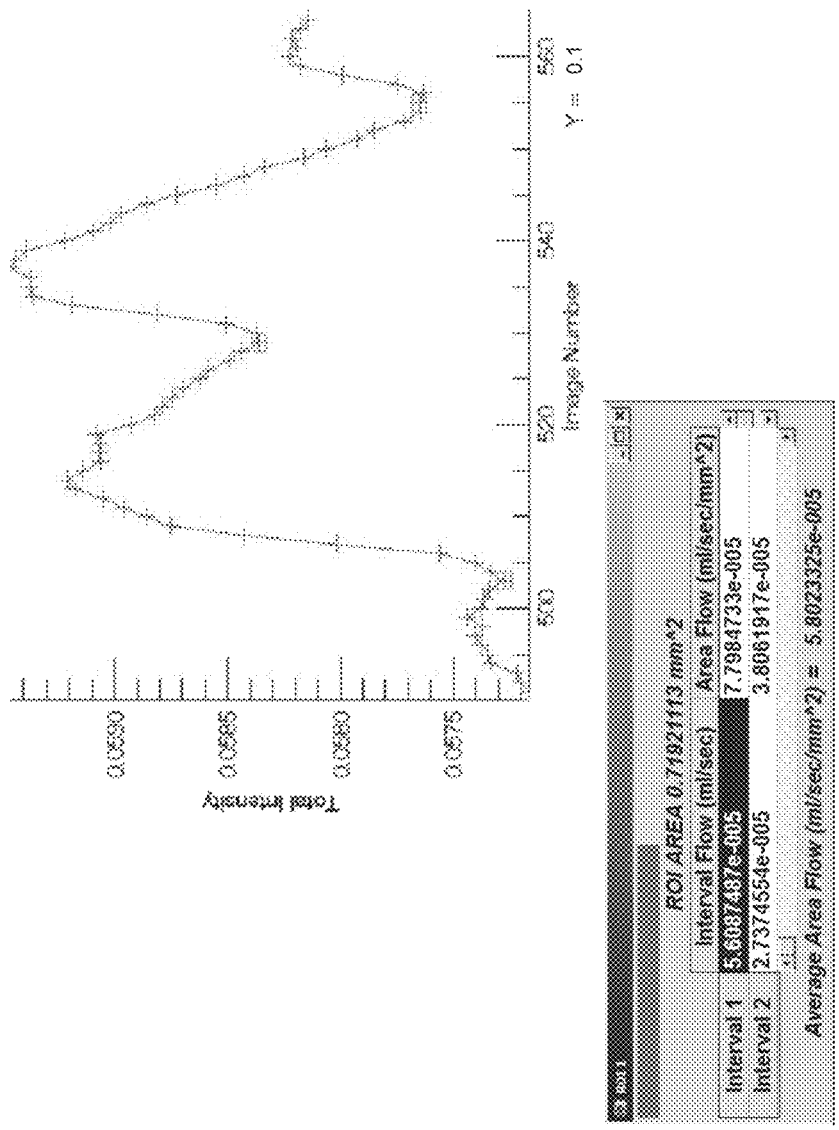
FIG. 24 shows FM-PPG data from a Rhesus monkey eye, and in particular, a plot generated for images 490-565, wherein the valleys between two consecutive blood flow pulses are selected (squares); the table indicates computed blood flow for each pulse as well as average flow.
Figure 25:
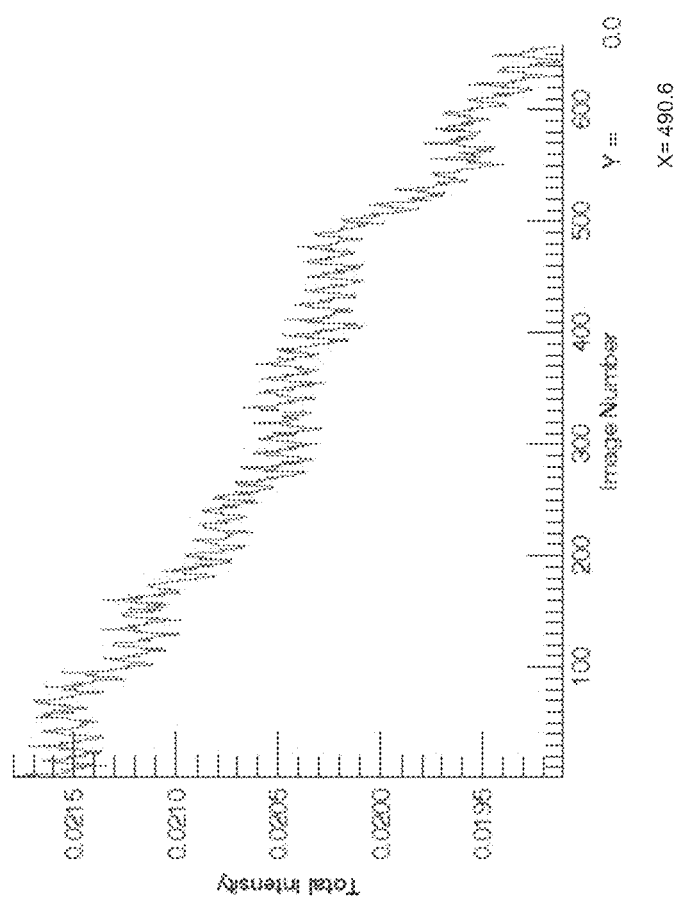
FIG. 25 shows a second angiogram sequence in connection with FM-PPG data from a Rhesus monkey eye.

A second plot was generated for images 490-565 was generated, and the valleys between two consecutive blood flow pulses were selected (green squares). At the same time, a table indicating computed blood flow for each pulse, as well as average flow (0.058 µL/sec/mm$^2$) was also generated as is shown in FIG. 24. Generally, the same procedure was followed for the second angiogram sequence shown in FIG. 25. From this plot, the subset of images 300-381 was selected, and the corresponding ICG dye concentration (C) was calculated based on the intensity of the pulses in this subset (0.0204), compared to the intensity of the peak brightness in the first sequence (0.0595, which corresponded to a 148 µM concentration). Thus, 148 µM/0.0595=C/0.0204, so C=50.7 µM.

Figure 26:
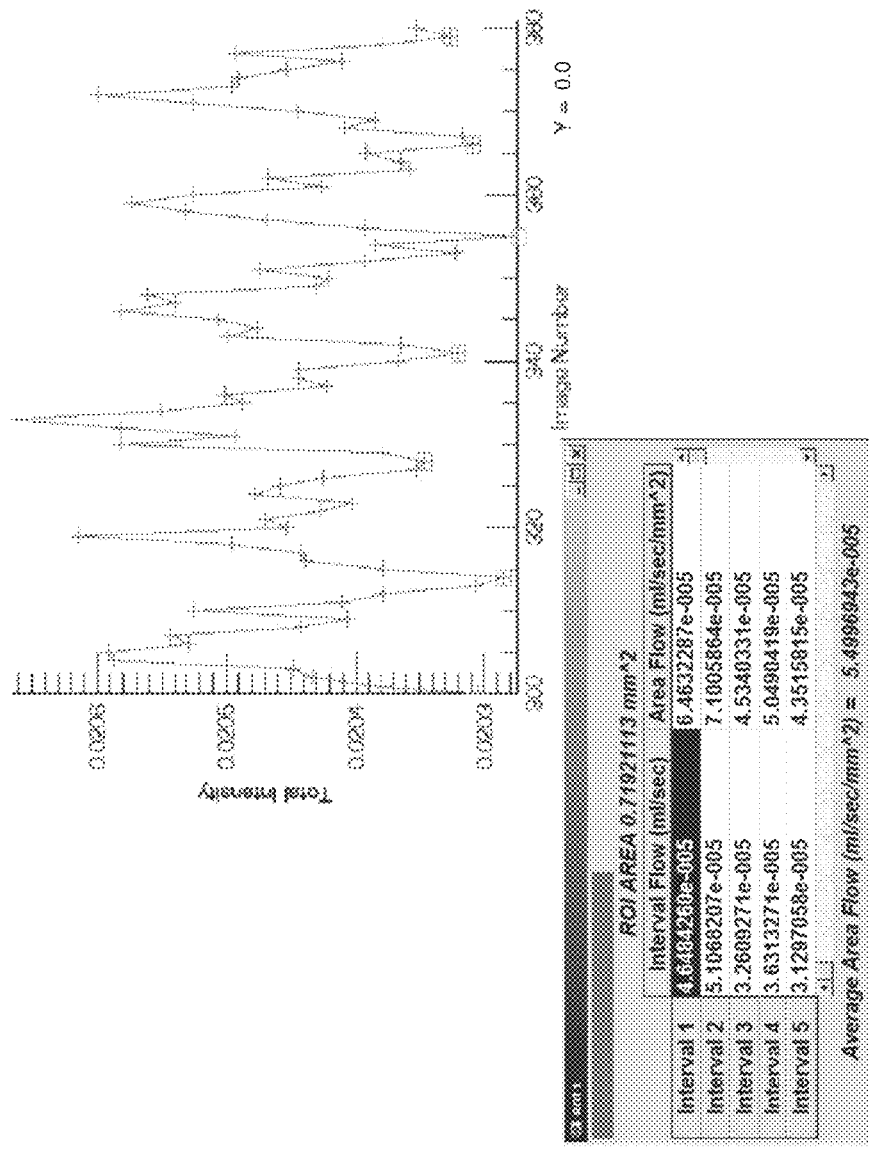
FIG. 26 shows a plot generated for images 300-381, wherein the valleys between five consecutive blood flow pulses are selected (squares); the table indicates computed blood flow for each pulse, as well as average flow.
Figure 27:
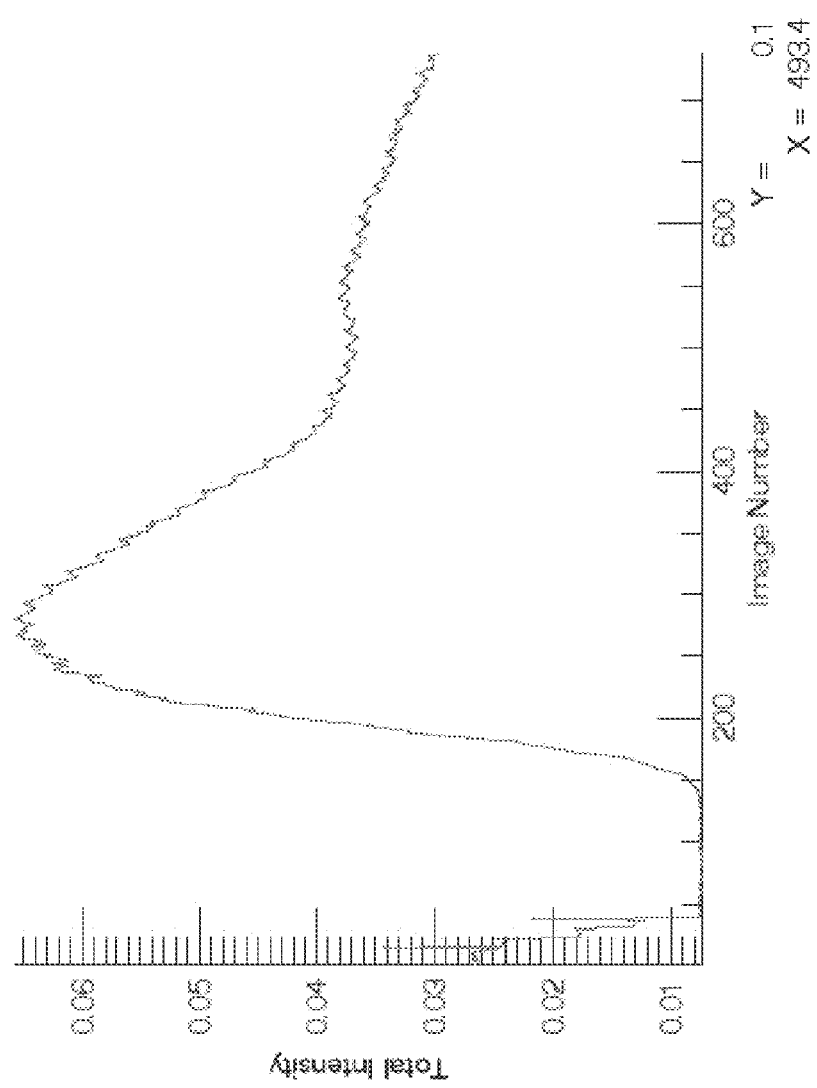
FIG. 27 shows a third angiogram sequence in connection with FM-PPG data from a Rhesus monkey eye.

The second plot was generated for images 300-381 was generated, and the valleys between five consecutive blood flow pulses were selected (squares). At the same time a table indicating computed blood flow for each pulse, as well as average flow (0.055 µL/sec/mm$^2$) was also generated as is shown in FIG. 26. Finally, the same procedure was applied to the third sequence, yielding the plots and table, wherein the plot is shown is FIG. 27.

Again, from that plot, it was determined the subsequence of images 260-290 were at peak brightness, and the concentration of ICG in circulating blood after dilution in transit was calculated. This time, the concentration of the ICG bolus injected was 25 mg/0.5 ml=50.0 mg/ml, which was diluted by 310 times, to a concentration of 0.161 mg/ml during its transit to the eye. Therefore, the peak concentration of dye in the ocular vessels (corresponding to images 260-290) was 207 µM.

Figure 28:
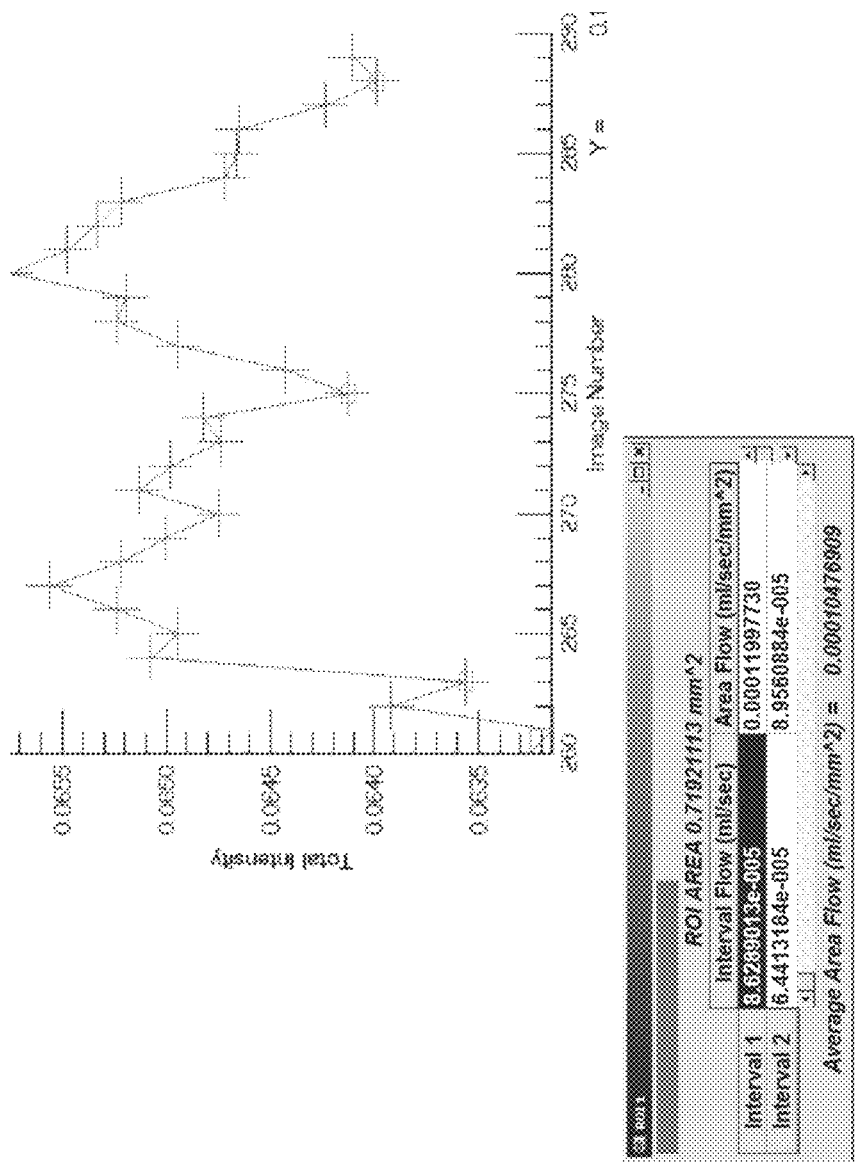
FIG. 28 shows a plot generated for images 260-290, wherein the valleys between two consecutive blood flow pulses are selected (squares); the table indicates computed blood flow for each pulse, as well as average flow.

The second plot was generated for images 260-290 was generated, and the valleys between two consecutive blood flow pulses were selected (green squares). At the same time the table indicating computed blood flow for each pulse, as well as average flow (0.105 µL/sec/mm$^2$) was also generated as is shown in FIG. 28.

The above analysis of three consecutive angiograms from the same eye yielded choroidal blood flows of 0.058, 0.055, and 0.105 µL/sec/mm$^2$, all of which compare favorably with the gold standard flow of 0.0866 μL/sec/mm$^2$, as reported by Alm and Bill and described in the following.

Figure 29B:
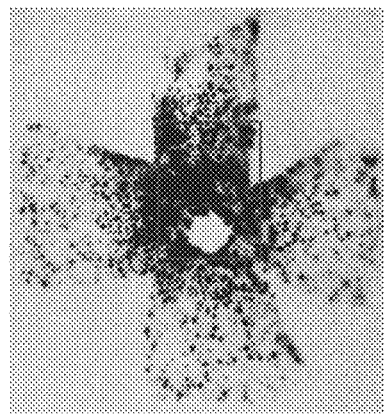
FIGS. 29A and 29B show an image from the human eye angiogram (29A) and the retinal area represented as a box superimposed upon the autoradiograph of a flat-mounted choroid from the left eye of one of the monkeys (29B) used by Alm and Bill as described in the specification.
Figure 29A:
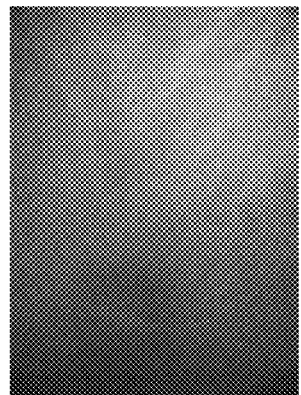

The left-hand image in FIG. 29A is an image from the human eye angiogram. In the right-hand image (FIG. 29B), the retinal area shown in the left-hand image (FIG. 29A) is represented as a box superimposed upon the autoradiograph of a flat-mounted choroid from the left eye of one of the monkeys used by Alm and Bill in their experiments. The hole in the middle is due to the removal of the optic nerve. The black spots represent the trapped microspheres, and the density of the spots is a measure of blood flow rate. The areas encompassed by the red box include the foveal and peripapillary regions, which according to their results from 17 subjects, have blood flows of 6.49 and 4.53 mg/min/mm$^2$, respectively. These data translate into an average flow rate of 0.866 μL/sec/mm$^2$ for the encompassed area.

While the present disclosure has been illustrated and described in connection with various embodiments shown and described in detail, it is not intended to be limited to the details shown, since various modifications and structural changes may be made without departing in any way from the scope of the present disclosure. Various modifications of form, arrangement of components, steps, details and order of operations of the embodiments illustrated, as well as other embodiments of the disclosure may be made without departing in any way from the scope of the present disclosure, and will be apparent to a person of skill in the art upon reference to this description. It is therefore contemplated that the appended claims will cover such modifications and embodiments as they fall within the true scope of the disclosure. For the terms "for example" and "such as," and grammatical equivalences thereof, the phrase "and without limitation" is understood to follow unless explicitly stated otherwise. As used herein, the singular forms "a", "an", and "the" include plural referents unless the context clearly dictates otherwise.

What is claimed is:

1. A method for quantifying absolute blood flow through a tissue volume, comprising:
    administering a volume of a fluorescence dye into the vasculature supplying the tissue volume;
    obtaining a sequence of angiographic images of the tissue volume;
    calculating average fluorescence intensities for the sequence of angiographic images of the tissue volume;
    generating a plot of time-varying average fluorescence intensity;
    determining an increase in thickness of a blood volume layer based on the plot of time-varying average fluorescence intensity and based on a graph of fluorescence intensity versus capillary diameter; and
    determining absolute blood flow based in part on the determined increase in thickness of the blood volume layer.

2. The method of claim 1, wherein determining the increase in thickness of the blood volume layer based on the plot of time-varying average fluorescence intensity and based on the graph of fluorescence intensity versus capillary diameter comprises:
    projecting an envelope defined by a minima and a maxima of PPG fluorescence-intensity oscillations of the plot onto the graph of fluorescence intensity versus capillary diameter;
    projecting the envelope from a curve of the graph onto an abscissa of the graph;
    determining the increase in thickness of the blood volume layer based on a width of the envelope when projected onto the abscissa.

3. The method of claim 1, wherein the fluorescence dye is indocyanine green (ICG).

4. The method of claim 1, wherein the fluorescence dye is administered at a concentration of between 25-50 mg/mL.

5. The method of claim 1, wherein the tissue volume comprises skin tissue.

6. The method of claim 1, wherein the angiographic images are obtained at a frame rate of 20-30 frames per second.

7. The method of claim 1, wherein the angiographic images are obtained by a fluorescence imaging system.

8. The method of claim 7, wherein the fluorescence imaging system comprises a laser for excitation of the fluorescence dye and a camera for capturing images of fluorescence emitted by the fluorescence dye.

9. The method of claim 1, wherein determining the increase in thickness of the blood volume layer based on the plot and based on the graph comprises making a first projection from the plot onto the graph.

10. The method of claim 9, wherein the first projection from the plot onto the graph is a projection of an envelope defined by a minima and a maxima of PPG fluorescence-intensity oscillations of the plot.

11. The method of claim 9, wherein determining the increase in thickness of the blood volume layer based on the plot and based on the graph comprises making a second projection from a curve of the graph onto an abscissa of the graph.

12. The method of claim 11, wherein:
    the first projection from the plot onto the graph is a projection of an envelope defined by a minima and a maxima of PPG fluorescence-intensity oscillations of the plot; and
    the second projection is a projection of the envelope from a curve of the graph onto an abscissa of the graph.

13. The method of claim 12, wherein determining the increase in thickness of the blood volume layer is based on a width of the envelope when projected onto the abscissa.

14. A system for quantifying absolute blood flow through a tissue volume, the system comprising one or more processors configured to execute instructions to cause the system to:
    obtain a sequence of angiographic images of a tissue volume following administration of a volume of a fluorescence dye into vasculature supplying the tissue volume;
    calculate average fluorescence intensities for the sequence of angiographic images of the tissue volume;
    generate a plot of time-varying average fluorescence intensity;
    determine an increase in thickness of a blood volume layer based on the plot of time-varying average fluorescence intensity and based on a graph of fluorescence intensity versus capillary diameter; and
    determine absolute blood flow based in part on the determined increase in thickness of the blood volume layer.

15. The system of claim 14, wherein determining the increase in thickness of the blood volume layer based on the plot of time-varying average fluorescence intensity and based on the graph of fluorescence intensity versus capillary diameter comprises:
    projecting an envelope defined by a minima and a maxima of PPG fluorescence-intensity oscillations of the plot onto the graph of fluorescence intensity versus capillary diameter;

projecting the envelope from a curve of the graph onto an abscissa of the graph;

determining the increase in thickness of the blood volume layer based on a width of the envelope when projected onto the abscissa.

16. The system of claim 14, wherein the angiographic images are obtained at a frame rate of 20-30 frames per second.

17. The system of claim 14, comprising a fluorescence imaging system configured to perform the obtaining the sequence of angiographic images.

18. The system of claim 17, wherein the fluorescence imaging system comprises a laser for excitation of the fluorescence dye and a camera for capturing images of fluorescence emitted by the fluorescence dye.

19. The system of claim 14, wherein determining the increase in thickness of the blood volume layer based on the plot and based on the graph comprises making a first projection from the plot onto the graph.

20. The system of claim 19, wherein the first projection from the plot onto the graph is a projection of an envelope defined by a minima and a maxima of PPG fluorescence-intensity oscillations of the plot.

21. The system of claim 19, wherein determining the increase in thickness of the blood volume layer based on the plot and based on the graph comprises making a second projection from a curve of the graph onto an abscissa of the graph.

22. The system of claim 21, wherein:
the first projection from the plot onto the graph is a projection of an envelope defined by a minima and a maxima of PPG fluorescence-intensity oscillations of the plot; and
the second projection is a projection of the envelope from a curve of the graph onto an abscissa of the graph.

23. The system of claim 22, wherein determining the increase in thickness of the blood volume layer is based on a width of the envelope when projected onto the abscissa.

24. A non-transitory computer-readable storage medium storing instructions for quantifying absolute blood flow through a tissue volume, the instructions configured to be executed by a system comprising one or more processors to cause the system to:
obtain a sequence of angiographic images of a tissue volume following administration of a volume of a fluorescence dye into vasculature supplying the tissue volume;
calculate average fluorescence intensities for the sequence of angiographic images of the tissue volume;
generate a plot of time-varying average fluorescence intensity;
determine an increase in thickness of a blood volume layer based on the plot of time-varying average fluorescence intensity and based on a graph of fluorescence intensity versus capillary diameter; and
determine absolute blood flow based in part on the determined increase in thickness of the blood volume layer.

25. The non-transitory computer-readable storage medium of claim 24, wherein determining the increase in thickness of the blood volume layer based on the plot of time-varying average fluorescence intensity and based on the graph of fluorescence intensity versus capillary diameter comprises:
projecting an envelope defined by a minima and a maxima of PPG fluorescence-intensity oscillations of the plot onto the graph of fluorescence intensity versus capillary diameter;
projecting the envelope from a curve of the graph onto an abscissa of the graph;
determining the increase in thickness of the blood volume layer based on a width of the envelope when projected onto the abscissa.

26. The non-transitory computer-readable storage medium of claim 24, wherein the angiographic images are obtained at a frame rate of 20-30 frames per second.

27. The non-transitory computer-readable storage medium of claim 24, wherein the system comprises a fluorescence imaging system configured to perform the obtaining the sequence of angiographic images.

28. The non-transitory computer-readable storage medium of claim 24, wherein the fluorescence imaging system comprises a laser for excitation of the fluorescence dye and a camera for capturing images of fluorescence emitted by the fluorescence dye.

29. The non-transitory computer-readable storage medium of claim 24, wherein determining the increase in thickness of the blood volume layer based on the plot and based on the graph comprises making a first projection from the plot onto the graph.

30. The non-transitory computer-readable storage medium of claim 29, wherein the first projection from the plot onto the graph is a projection of an envelope defined by a minima and a maxima of PPG fluorescence-intensity oscillations of the plot.

31. The non-transitory computer-readable storage medium of claim 29, wherein determining the increase in thickness of the blood volume layer based on the plot and based on the graph comprises making a second projection from a curve of the graph onto an abscissa of the graph.

32. The non-transitory computer-readable storage medium of claim 31, wherein:
the first projection from the plot onto the graph is a projection of an envelope defined by a minima and a maxima of PPG fluorescence-intensity oscillations of the plot; and
the second projection is a projection of the envelope from a curve of the graph onto an abscissa of the graph.

33. The non-transitory computer-readable storage medium of claim 32, wherein determining the increase in thickness of the blood volume layer is based on a width of the envelope when projected onto the abscissa.

* * * * *